United States Patent
Yan et al.

(10) Patent No.: US 9,192,786 B2
(45) Date of Patent: Nov. 24, 2015

(54) REAL-TIME, ON-LINE AND OFFLINE TREATMENT DOSE TRACKING AND FEEDBACK PROCESS FOR VOLUMETRIC IMAGE GUIDED ADAPTIVE RADIOTHERAPY

(75) Inventors: Di Yan, Auburn Hills, MI (US); Alvaro Martinez, Bloomfield Hills, MI (US)

(73) Assignee: William Beaumont Hospital, Royal Oak, MI (US)

( * ) Notice: Subject to any disclaimer, the term of this patent is extended or adjusted under 35 U.S.C. 154(b) by 0 days.

(21) Appl. No.: 11/805,716

(22) Filed: May 24, 2007

(65) Prior Publication Data

US 2008/0031406 A1 Feb. 7, 2008

Related U.S. Application Data

(60) Provisional application No. 60/808,343, filed on May 25, 2006, provisional application No. 60/881,092, filed on Jan. 18, 2007.

(51) Int. Cl.
*A61N 5/10* (2006.01)

(52) U.S. Cl.
CPC ............... *A61N 5/1049* (2013.01); *A61N 5/107* (2013.01); *A61N 5/1037* (2013.01); *A61N 5/1067* (2013.01); *A61N 5/1071* (2013.01); *A61N 2005/1054* (2013.01); *A61N 2005/1061* (2013.01);
(Continued)

(58) Field of Classification Search
CPC . A61N 5/1037; A61N 5/1049; A61N 5/1067; A61N 5/107; A61N 5/1071; A61N 2005/1054; A61N 2005/1061; A61N 2005/1062; A61N 2005/1072; B65H 19/20; B65H 19/28; B65H 19/283; B65H 75/10; B65H 75/28
USPC .................. 378/4, 8, 9, 11, 16, 19, 20, 64, 65, 378/147–153, 195–198
See application file for complete search history.

(56) References Cited

U.S. PATENT DOCUMENTS 3,778,614 A  12/1973  Hounsfield
3,780,291 A  12/1973  Stein et al.
(Continued)

FOREIGN PATENT DOCUMENTS

CN      1419891       5/2003
CN      1424925 A     6/2003
(Continued)

OTHER PUBLICATIONS

U.S. Appl. No. 11/786,781, filed Apr. 12, 2007, Tiezhi Zhang.
(Continued)

*Primary Examiner* — Toan Ton
*Assistant Examiner* — Mona M Sanei
(74) *Attorney, Agent, or Firm* — Honigman Miller Schwartz and Cohn LLP; Douglas H. Siegel; Jonthan P. O'Brien

(57) ABSTRACT

A method of treating an object with radiation that includes generating volumetric image data of an area of interest of an object and emitting a therapeutic radiation beam towards the area of interest of the object in accordance with a reference plan. The method further includes evaluating the volumetric image data and at least one parameter of the therapeutic radiation beam to provide a real-time, on-line or off-line evaluation and on-line or off-line modification of the reference plan.

88 Claims, 9 Drawing Sheets

(52) U.S. Cl.
CPC . *A61N2005/1062* (2013.01); *A61N 2005/1072* (2013.01)

(56) References Cited

U.S. PATENT DOCUMENTS

| | | | |
|---|---|---|---|
| 4,132,895 A | 1/1979 | Froggatt | |
| 4,145,613 A | 3/1979 | Bunch | |
| 4,304,999 A | 12/1981 | Richey et al. | |
| 4,315,157 A | 2/1982 | Barnes | |
| 4,380,818 A | 4/1983 | Pfeiler | |
| 4,389,569 A | 6/1983 | Hattori et al. | |
| 4,405,745 A | 9/1983 | Mathis et al. | |
| 4,414,682 A | 11/1983 | Annis et al. | |
| 4,534,051 A | 8/1985 | Grady et al. | |
| 4,547,892 A | 10/1985 | Richey et al. | |
| 4,712,226 A | 12/1987 | Horbaschek | |
| 4,920,552 A | 4/1990 | Hermens | |
| 5,039,867 A | 8/1991 | Nishihara et al. | |
| 5,125,012 A | 6/1992 | Schittenhelm | |
| 5,157,707 A | 10/1992 | Ohlson | |
| 5,214,686 A | 5/1993 | Webber | |
| 5,335,255 A | 8/1994 | Seppi et al. | |
| 5,379,333 A | 1/1995 | Toth | |
| 5,394,452 A | 2/1995 | Swerdloff et al. | |
| 5,411,026 A | 5/1995 | Carol | |
| 5,485,494 A | 1/1996 | Williams et al. | |
| 5,521,957 A | 5/1996 | Hansen | |
| 5,533,082 A | 7/1996 | Gronemeyer | |
| 5,602,892 A | 2/1997 | Llacer | |
| 5,625,661 A | 4/1997 | Oikawa | |
| 5,657,364 A | 8/1997 | Pfoh | |
| 5,661,773 A | 8/1997 | Swerdloff et al. | |
| 5,663,995 A | 9/1997 | Hu | |
| 5,675,625 A | 10/1997 | Rockseisen | |
| 5,699,805 A | 12/1997 | Seward et al. | |
| 5,719,914 A | 2/1998 | Rand et al. | |
| 5,724,400 A | 3/1998 | Swerdloff | |
| 5,748,700 A | 5/1998 | Shepherd et al. | |
| 5,751,781 A | 5/1998 | Brown et al. | |
| 5,754,622 A | 5/1998 | Hughes | |
| 5,835,558 A | 11/1998 | Maschke | |
| 5,848,126 A | 12/1998 | Fujita et al. | |
| 5,864,597 A | 1/1999 | Kobayashi | |
| 5,877,501 A | 3/1999 | Ivan et al. | |
| 5,912,943 A | 6/1999 | Deucher et al. | |
| 5,929,449 A | 7/1999 | Huang | |
| 5,949,811 A | 9/1999 | Baba et al. | |
| 5,966,422 A | 10/1999 | Dafni et al. | |
| 5,999,587 A | 12/1999 | Ning et al. | |
| 6,031,888 A | 2/2000 | Ivan et al. | |
| 6,041,097 A | 3/2000 | Roos et al. | |
| 6,113,264 A | 9/2000 | Watanabe | |
| 6,148,058 A | 11/2000 | Dobbs | |
| 6,152,598 A | 11/2000 | Tomisaki et al. | |
| 6,200,024 B1 | 3/2001 | Negrelli | |
| 6,229,870 B1 | 5/2001 | Morgan | |
| 6,239,439 B1* | 5/2001 | Itabashi et al. ........... 250/370.11 | |
| 6,256,370 B1 | 7/2001 | Yavuz | |
| 6,259,766 B1 | 7/2001 | Cuppen | |
| 6,269,143 B1 | 7/2001 | Tachibana | |
| 6,285,739 B1 | 9/2001 | Rudin et al. | |
| 6,292,534 B1 | 9/2001 | Linders et al. | |
| 6,298,115 B1 | 10/2001 | Nilsson | |
| 6,307,914 B1 | 10/2001 | Kunieda et al. | |
| 6,318,892 B1 | 11/2001 | Suzuki et al. | |
| 6,325,537 B1 | 12/2001 | Watanabe | |
| 6,345,114 B1 | 2/2002 | Mackie et al. | |
| 6,385,286 B1* | 5/2002 | Fitchard et al. ................ 378/65 | |
| 6,385,288 B1 | 5/2002 | Kanematsu | |
| 6,389,104 B1 | 5/2002 | Bani-Hashemi et al. | |
| 6,393,096 B1 | 5/2002 | Carol et al. | |
| 6,435,715 B1 | 8/2002 | Betz et al. | |
| 6,463,122 B1 | 10/2002 | Moore | |
| 6,546,073 B1 | 4/2003 | Lee | |
| 6,560,311 B1 | 5/2003 | Shepard et al. | |
| 6,582,121 B2 | 6/2003 | Crain et al. | |
| 6,618,466 B1 | 9/2003 | Ning | |
| 6,628,745 B1 | 9/2003 | Annis et al. | |
| 6,633,627 B2 | 10/2003 | Horiuchi | |
| 6,661,870 B2 | 12/2003 | Kapatoes et al. | |
| 6,707,876 B2 | 3/2004 | Tanigawa | |
| 6,760,402 B2 | 7/2004 | Ghelmansarai | |
| 6,792,074 B2* | 9/2004 | Erbel et al. ...................... 378/65 | |
| 6,842,502 B2* | 1/2005 | Jaffray et al. ................... 378/65 | |
| 6,865,254 B2 | 3/2005 | Näfstadius | |
| 6,888,919 B2 | 5/2005 | Graf | |
| 6,907,100 B2 | 6/2005 | Taguchi | |
| 6,915,005 B1 | 7/2005 | Ruchala et al. | |
| 6,980,627 B2 | 12/2005 | Qiu et al. | |
| 6,990,175 B2 | 1/2006 | Nakashima et al. | |
| 6,993,112 B2* | 1/2006 | Hesse ............................. 378/65 | |
| 7,030,386 B2 | 4/2006 | Pang et al. | |
| 7,062,006 B1 | 6/2006 | Pelc et al. | |
| 7,072,436 B2 | 7/2006 | Pelc | |
| 7,127,035 B2 | 10/2006 | Anno et al. | |
| 7,145,981 B2 | 12/2006 | Pelc | |
| 7,154,991 B2 | 12/2006 | Earnst et al. | |
| 7,170,975 B2 | 1/2007 | Distler et al. | |
| 7,193,227 B2 | 3/2007 | Hiramoto et al. | |
| 7,227,923 B2 | 6/2007 | Edic et al. | |
| 7,227,925 B1 | 6/2007 | Mansfield et al. | |
| 7,280,631 B2 | 10/2007 | DeMan et al. | |
| 7,305,063 B2 | 12/2007 | Heuscher | |
| 7,388,940 B1 | 6/2008 | DeMan et al. | |
| 7,428,292 B2 | 9/2008 | DeMan et al. | |
| 7,471,765 B2 | 12/2008 | Jaffray et al. | |
| 7,496,181 B2 | 2/2009 | Mazin et al. | |
| 7,657,304 B2 | 2/2010 | Mansfield et al. | |
| 7,760,849 B2 | 7/2010 | Zhang | |
| 7,826,592 B2 | 11/2010 | Jaffray et al. | |
| 7,945,021 B2 | 5/2011 | Shapiro et al. | |
| 8,073,104 B2 | 12/2011 | Yan et al. | |
| 2003/0072407 A1 | 4/2003 | Mihara et al. | |
| 2003/0095627 A1 | 5/2003 | Anderton | |
| 2003/0138077 A1* | 7/2003 | Lee ................................ 378/65 | |
| 2003/0191363 A1 | 10/2003 | Boll et al. | |
| 2003/0235271 A1 | 12/2003 | Rand | |
| 2004/0002641 A1 | 1/2004 | Sjogren et al. | |
| 2004/0042583 A1 | 3/2004 | Wackerle et al. | |
| 2004/0081270 A1 | 4/2004 | Heuscher | |
| 2004/0086074 A1 | 5/2004 | Taguchi | |
| 2004/0096033 A1 | 5/2004 | Seppi et al. | |
| 2004/0120452 A1 | 6/2004 | Shapiro et al. | |
| 2004/0165696 A1 | 8/2004 | Lee | |
| 2004/0174949 A1* | 9/2004 | Yamashita et al. .............. 378/65 | |
| 2004/0184578 A1 | 9/2004 | Nakano | |
| 2004/0254448 A1 | 12/2004 | Amies et al. | |
| 2005/0013404 A1 | 1/2005 | Kasperl et al. | |
| 2005/0027196 A1 | 2/2005 | Fitzgerald | |
| 2005/0053189 A1 | 3/2005 | Gohno et al. | |
| 2005/0054937 A1 | 3/2005 | Takaoka et al. | |
| 2005/0058237 A1 | 3/2005 | Morf | |
| 2005/0080336 A1 | 4/2005 | Byrd et al. | |
| 2005/0085710 A1 | 4/2005 | Earnst et al. | |
| 2005/0111610 A1 | 5/2005 | DeMan et al. | |
| 2005/0111616 A1 | 5/2005 | Li et al. | |
| 2005/0111621 A1 | 5/2005 | Riker et al. | |
| 2005/0197564 A1 | 9/2005 | Dempsey | |
| 2005/0234327 A1 | 10/2005 | Saracen et al. | |
| 2005/0249432 A1 | 11/2005 | Zou et al. | |
| 2005/0251029 A1* | 11/2005 | Khamene et al. ............. 600/427 | |
| 2006/0002506 A1 | 1/2006 | Pelc | |
| 2006/0008047 A1 | 1/2006 | Zhou et al. | |
| 2006/0017009 A1 | 1/2006 | Rink et al. | |
| 2006/0067468 A1 | 3/2006 | Rietzel | |
| 2006/0239409 A1 | 10/2006 | Levene et al. | |
| 2006/0245543 A1* | 11/2006 | Earnst et al. .................... 378/65 | |
| 2006/0259282 A1 | 11/2006 | Failla et al. | |
| 2006/0269049 A1 | 11/2006 | Yin et al. | |
| 2006/0274885 A1 | 12/2006 | Wang et al. | |
| 2006/0285639 A1 | 12/2006 | Olivera et al. | |
| 2006/0285640 A1 | 12/2006 | Nizin et al. | |
| 2006/0285641 A1 | 12/2006 | Scherch | |
| 2007/0003123 A1 | 1/2007 | Fu et al. | |

(56) References Cited

U.S. PATENT DOCUMENTS

| | | | |
|---|---|---|---|
| 2007/0016014 A1 | 1/2007 | Hara et al. | |
| 2007/0019782 A1 | 1/2007 | Van Stevendaal et al. | |
| 2007/0053492 A1* | 3/2007 | Kidani et al. | 378/65 |
| 2007/0076846 A1* | 4/2007 | Ruchala et al. | 378/65 |
| 2007/0280408 A1* | 12/2007 | Zhang | 378/10 |
| 2008/0031406 A1 | 2/2008 | Yan et al. | |
| 2010/0008467 A1 | 1/2010 | Dussault et al. | |
| 2010/0054410 A1 | 3/2010 | Nord et al. | |
| 2010/0119032 A1 | 5/2010 | Yan et al. | |
| 2010/0135454 A1 | 6/2010 | Noo | |
| 2011/0002439 A1 | 1/2011 | Zhang | |
| 2011/0080992 A1 | 4/2011 | Dafni | |
| 2011/0211666 A1 | 9/2011 | Ying et al. | |

FOREIGN PATENT DOCUMENTS

| | | |
|---|---|---|
| CN | 1589744 A | 3/2005 |
| CN | 1723743 A | 1/2006 |
| CN | 1748217 | 3/2006 |
| CN | 1758876 | 4/2006 |
| DE | 1992708 U | 8/1968 |
| DE | 2822241 A1 | 12/1978 |
| EP | 0314231 A2 | 5/1989 |
| EP | 0922943 A2 | 6/1999 |
| JP | 5252594 | 4/1977 |
| JP | 56101579 A | 8/1981 |
| JP | 56168578 A | 12/1981 |
| JP | 58-94835 A | 6/1983 |
| JP | 58163341 A | 9/1983 |
| JP | 4242736 A | 8/1992 |
| JP | 4-307035 | 10/1992 |
| JP | 5172764 A | 7/1993 |
| JP | 6030926 A | 2/1994 |
| JP | 6277205 A | 10/1994 |
| JP | 07-255717 A | 10/1995 |
| JP | 08122438 A | 5/1996 |
| JP | 09-218939 A | 8/1997 |
| JP | 09327453 A | 12/1997 |
| JP | 10-033520 A | 2/1998 |
| JP | 10-113400 A | 5/1998 |
| JP | 10-511595 A | 11/1998 |
| JP | 10295683 A | 11/1998 |
| JP | 10-328318 A | 12/1998 |
| JP | 11-047290 | 2/1999 |
| JP | 11-99148 A | 4/1999 |
| JP | 11-160440 A | 6/1999 |
| JP | 11-276463 | 10/1999 |
| JP | 2000126164 A | 5/2000 |
| JP | 2000176029 A | 6/2000 |
| JP | 2000308634 A | 11/2000 |
| JP | 2002210028 A | 7/2002 |
| JP | 2003210596 A | 7/2003 |
| WO | 97/13552 A1 | 4/1997 |
| WO | 98/52635 A1 | 11/1998 |
| WO | 99/03397 A1 | 1/1999 |
| WO | WO0160236 A2 | 8/2001 |
| WO | WO2004061744 A2 | 7/2004 |
| WO | WO2004061864 A2 | 7/2004 |
| WO | WO2004080309 A2 | 9/2004 |
| WO | 2006/018761 A1 | 2/2006 |
| WO | WO2006034973 A1 | 4/2006 |

OTHER PUBLICATIONS

Yan D., et al., "A New Model for 'Accept or Reject' Strategies in On-Line and Off-Line Treatment Evaluation," International Journal of Radiation Oncology, Biology Physics, vol. 31, No. 4, 1995, pp. 943-952.

Yan D., et al., "Adaptive Radiation Therapy," Phys. Med. Biol., vol. 42, 1997, pp. 123-132.

Yan D., et al., "The Use of Adaptive Radiation Therapy to Reduce Setup Error: A Prospective Clinical Study," Int. J. Radiation Oncology Biol. Phys., vol. 41, No. 3, 1998, pp. 715-720.

Yan D., et al., "Adaptive Modification of Treatment Planning to Minimize the Deleterious Effects of Treatment Setup Errors," Int. J. Radiation Oncology Biol. Phys., vol. 37, No. 5, while the publication date is unknown, it is believed to have been published prior to 1999, pp. 1-27.

Yan D., et al., "A Model to Accumulate Fractionated Dose in a Deforming Organ," Int. J. Radiation Oncology Biol. Phys., vol. 44, No. 3, 1999, pp. 665-675.

Lockman D., et al., "Estimating the Dose Variation in a Volume of Interest with Explicit Consideration of Patient Geometric Variation," Med. Phys., vol. 27, No. 9, Sep. 2000, pp. 2100-2108.

Yan D., et al., "An Off-Line Strategy for Constructing a Patient-Specific Planning Target Volume for Image Guided Adaptive Radiotherapy of Prostate Cancer," Int. J. Radiation Oncology Biol. Phys., vol. 48, No. 1, 2000, pp. 289-302.

Yan D., "Treatment Strategy for Daily Image Feedback Adaptive Radiotherapy," Proceeding, XIIIth International Conference on the Use of Computers in Radiotherapy, Heidelberg, Germany, 2000, pp. 518-520.

Yan D. et al. "Organ/Patient Geometric Variation in External Beam Radiotherapy and Its Effect," Med. Phys., vol. 28, No. 4, Apr. 2001, pp. 593-602.

Yan D., et al., Strategies for Off-Line and On-Line Image Feedback Adaptive Radiotherapy, Editors: BK Paliwal, DE Herbert, JF Fowler, MP Mehta, Biological & Physical Basis of IMRT & Tomotherapy, AAPM Symposium Proceeding No. 12, 2002, pp. 139-150.

Birkner M., et al., "Adapting Inverse Planning to Patient and Organ Geometrical Variation: Algorithm and Implementation," Med. Phys., vol. 30, No. 10, Oct. 2003, pp. 2822-2831.

Liang J., et al., "Reducing Uncertainties in Volumetric Image Based Deformable Organ Registration," Med. Phys., vol. 30, No. 8, Aug. 2003, pp. 2116-2122.

Ghilezan M., et al., "Online Image-Guided Intensity-Modulated Radiotherapy for Prostate Cancer: How Much Improvement Can We Expect? A Theoretical Assessment of Clinical Benefits and Potential Dose Escalation by Improving Precision and Accuracy of Radiation Delivery," Int. J. Radiation Oncology Biol. Phys., vol. 60, No. 5, 2004, pp. 1602-1610.

Weinberg R.., et al., "Dosimetric Uncertainties of Three-Dimensional Dose Reconstruction from Two-Dimensional Data in a Multi-Institutional Study," Journal of Applied Clinical Medical Physics, vol. 5, No. 4, Fall 2004, pp. 15-28.

Söhn M. et al., "Modeling Individual Geometric Variation Based on Dominant Eigenmodes of Organ Deformation: Implementation and Evaluation," Phys Med Biol, vol. 50, 2005, pp. 5893-5908.

Yan D., et al., "Computed Tomography Guided Management of Interfractional Patient Variation," Semin. Radiat. Oncol. vol. 15, 2005, pp. 168-179.

Yan D., "Image-Guided/Adaptive Radiotherapy," Medical Radiology-Radiation Oncology, Volume: New Technologies in Radiation Oncology, Edited by W. Schlegel, T. Bortfeld and AL Grosu, Springer-Verlag, Berlin, Heidelberg, New York, Hong Kong, Sep. 8, 2005, ISBN 3-540-00321-5, pp. 317-332.

Chen, J., et al., "Dose-Guided Radiation Therapy with Megavoltage Cone-Beam CT," published by The British Journal of Radiology, vol. 79, 2006, pp. S87-S98.

Chi Y., et al., "A Material Sensitivity Study on the Accuracy of Deformable Organ Registration Using Linear Biomechanical Models," Med. Phys., vol. 33: No. 2, Feb. 2006, pp. 421-433.

Kessler, M.L., "Image Registration and Data Fusion in Radiation Therapy," The British Journal of Radiology, vol. 79, 2006, pp. S99-S108.

Yan D., "Image-Guided Adaptive Radiotherapy Model," AAPM, Mar. 10, 2006, pp. 1-15.

Zhang T., et al., "Automatic Delineation of Online Head and Neck CT Images: Towards Online Adaptive Radiotherapy," Int. J. of Radiation Oncology Biol. Phys., vol. 68, No. 2, 2007, pp. 522-530.

Kapatoes, J.M., et al., "On the Accuracy and Effectiveness of Dose Reconstruction for Tomotherapy," Phys. Med. Biol., vol. 46, 2001, pp. 943-966.

Schaly, B., et al., "Tracking the Dose Distribution in Radiation Therapy by Accounting for Variable Anatomy," Phys. Med. Biol., vol. 49, 2004, pp. 791-805.

(56) References Cited

OTHER PUBLICATIONS

Yong, Y., et al., "Evaluation of On-Board kV Cone Beam CT (CBCT)-based Dose Calculation," Phys. Med. Biol., vol. 52, 2007, pp. 685-705.
Mueller, K., et al., "Cone-Beam Computed Tomography (CT) for a Megavoltage Linear Accelerator (LINAC) Using an Electronic Portal Imaging Device (EPID) and the Algebraic Reconstruction Technique (ART)," publication source unknown, (publication date unknown), 4 pages, while the date of publication is unknown, it is believe that the article was publicly available before May 24, 2007.
Yan D., "Adapt Radiotherapy to Temporal Biological Targets Assessed Using Biological Images," publication source unknown, while the date of publication is unknown, it is believe that the article was publicly available before May 24, 2007, 3 pages.
Antonuk, L.E., et al., "A Real-Time, Flat-Panel, Amorphous Silicon, Digital X-Ray Imager", Radiographics, vol. 15, No. 4, Jul. 1995, pp. 993-1000.
Antonuk, L.E., et al., "Initial Performance Evaluation of an Indirect-Detection, Active Matrix Flat-Panel Imager (AMPFI) Prototype for Megavoltage Imaging", Int. J. Radiat. Oncol. Biol. Phys., vol. 42, No. 2, 1998, pp. 437-454.
Antonuk, L.E., et al., "Megavoltage Imaging with a Large-Area, Flat-Panel, Amorphous Silicon Imager", Int. J. Radiat. Oncol. Biol. Phys., vol. 36, No. 3, 1996, pp. 661-672.
Antonuk, L.E., et al., "Strategies to Improve the Signal and Noise Performance of Active Matrix, Flat-Panel Imagers for Diagnostic X-Ray Applications", Med. Phys., vol. 27, No. 2, Feb. 2000, pp. 289-306.
Basset, P.G., Wong, J.W. and Aspin, N.: "An Interactive Computer System for Studying Human Mucociliary Clearance", Computer Biol. Med. 1979, vol. 9, pp. 97-105.
Bissonnette, J.P., et al., "Optimal Radiographic Magnification for Portal Imaging.", Med. Phys., vol. 21, No. 9, Sep. 1994, pp. 1435-1445.
Boyer, A.L., et al., (IMRT Collaborative Working Group): "Intensity-modulated radiotherapy: Current status and issues of interest", Int. J. Radiat. Oncol. Biol. Phys. 2001, vol. 51, No. 4, pp. 880-914.
Boyer, A.L., et al., "A Review of Electronic Portal Imaging Devices (EPIDs)", Medical Physics, Jan./Feb. 1992, vol. 19, No. 1, pp. 19: 1-16.
Brown, A.P., et al., "Three-Dimensional Photon Treatment Planning for Hodgkin's Disease", Int. J. Radiat. Oncol. Biol. Phys., May 15, 1991, vol. 21, No. 1, pp. 205-215.
Cheng, A., et al., "Systematic Verification of a Three-Dimensional Electron Beam Dose Calculation Algorithm", Med. Phys., 1996, vol. 23, No. 5, pp. 685-693.
Cullity, B.D., "Elements of X-Ray Diffraction, Second Edition," (Reading, MA: Addison Wesley, 1978), p. 6-12.
Dieu, L., et al., "Ion Beam Sputter-Deposited SiN/TiN Attenuating Phase-Shift Photoblanks," publication source and date unknown, 8 pages.
Drake, D.G., et al., "Characterization of Fluoroscopic Imaging System for kV and MV Radiography", Med. Phys., May 2000, vol. 27, No. 5, pp. 898-905.
Du, M.N., et al., "A Multileaf Collimator Field Prescription Preparation System for Conventional Radiotherapy", Int. J. Radiat. Oncol. Biol. Phys., 1994, vol. 30, No. 3, pp. 707-714.
Du, M.N., et al., "A Multileaf Collimator Field Prescription Preparation System for Conventional Radiotherapy", Int. J. Radiat. Oncol. Biol. Phys., 1995, vol. 32, No. 2, pp. 513-520.
El-Mohri, Y., et al., "Relative Dosimetry Using Active Matrix Flat-Panel Imager (AMFPI) Technology", Med. Phys., Aug. 1999, vol. 26, No. 8, pp. 1530-1541.
EP Search Report for Application 07755309.7 dated Apr. 15, 2011.
Ezz, A., et al., "Daily Monitoring and Correction of Radiation Field Placement Using a Video-Based Portal Imaging System: a Pilot Study", Int. J. Radiat. Oncol. Biol. Phys., 1992, vol. 22, No. 1, pp. 159-165.
Frazier, A., et al., "Dosimetric Evaluation of the Conformation of the Multileaf Collimator to Irregularly Shaped Fields", Int. J. Radiat. Oncol.Biol. Phys., 1995, vol. 33, No. 5, pp. 1229-1238.
Frazier, A., et al., "Effects of Treatment Setup Variation on Beam's Eye View Dosimetry for Radiation Therapy Using the Multileaf Collimator vs. The Cerrobend Block", Int. J. Radiat. Oncol. Biol. Phys., 1995, vol. 33, No. 5, pp. 1247-1256.
Graham, M.L., et al., "A Method to Analyze 2-Dimensional Daily Radiotherapy Portal Images from an On-Line Fiber-Optic Imaging System.", Int. J. Radiat. Oncol. Biol. Phys., Mar. 1991, vol. 20, No. 3, pp. 613-619.
Gupta, N.K., et al, Tangential CT, A Computed Tomography Method Developed for Industrial Rotating Slat Collimator, 16th WCNDT 2004, Sep. 2004, five pages.
Halverson, K.J., et al., "Study of Treatment Variation in the Radiotherapy of Head and Neck Tumors Using a Fiber-Optic On-Line Line Radiotherapy Imaging System", Int. J. Radiat. Oncol. Biol. Phys., Oct. 1991, vol. 21, No. 5, pp. 1327-1336.
Harms, W.B., Sr., et al., "A Software Tool for the Quantitative Evaluation of 3D Dose Calculation Algorithms", Med. Phys., Oct. 1998, vol. 25, No. 10, pp. 1830-1839.
Herman, M.G., et al. "Clinical use of electronic portal imaging: Report of AAPM Radiation Therapy Committee Task Group 58", Med. Phys. May 2001, vol. 28, No. 5, pp. 712-737.
Jaffray, et al., Cone-Beam CT: Applications in Image-Guided External Beam Radiotherapy and Brachytherapy, publication source unknown, date unknown, one page.
Jaffray, et al., "Conebeam Tomographic Guidance of Radiation Field Placement for Radiotherapy of the Prostate," Manuscript accepted for publication in the International Journal of Radiation Oncology, Biology, Oct. 1998, 32 pages.
Jaffray, et al., "Exploring 'Target of the Day' Strategies for a Medical Linear Accelerator with Conebeam-CT Scanning Capability," XIIth ICCR held in Salt Lake City, Utah, May 27-30, 1997, pp. 172-174.
Jaffray, et al., "Flat-Panel Cone-Beam CT for Image-Guided External Beam Radiotherapy," publication source unknown, Oct. 1999, 36 pages.
Jaffray, et al., "Managing Geometric Uncertainty in Conformal Intensity-Modulated Radiation Therapy," Seminars in Radiation Oncology, vol. 9, No. 1, Jan. 1999 pp. 4-19.
Jaffray, et al., "Performance of a Volumetric CT Scanner Based Upon a Flat-Panel Imager," SPIE Physics of Medical Imaging, vol. 3659, Feb. 1999, pp. 204-214.
Jaffray, D.A., et al., "A Radiographic and Tomographic Imaging System Integrated into a Medical Linear Accelerator for Localization of Bone and Soft-Tissue Targets", Int. J. Radiat. Oncol. Biol. Phys., 1999, vol. 45, No. 3, pp. 773-789.
Jaffray, D.A., et al., "Activity Distribution of a Cobalt-60 Teletherapy Source", Med. Phys., Mar./Apr. 1991, vol. 18, No. 2, pp. 288-291.
Jaffray, D.A., et al., "Cone-Beam Computed Tomography with a Flat-Panel Imager: Initial Performance Characterization", Med. Phys. Jun. 2000, vol. 27, No. 6, pp. 1311-1323.
Jaffray, D.A., et al., "Dual-Beam Imaging for Online Verification of Radiotherapy Field Placement", Int. J. Radiat. Oncol. Biol. Phys., 1995, vol. 33, No. 5, pp. 1273-1280.
Jaffray, D.A., et al., "X-Ray Scatter in Megavoltage Transmission Radiography: Physical Characteristics and Influence on Image Quality", Med. Phys., Jan. 1994, vol. 21, No. 1, pp. 45-60.
Jaffray, D.A., et al., "X-Ray Sources of Medical Linear Accelerators: Focal and Extra-Focal Radiation", Med. Phys. Sep./Oct. 1993, vol. 20, No. 5, pp. 1417-1427.
Jaffray, et al., "Cone-Beam Computed Tomography with a Flat-Panel Imager: Initial Performance Characterization," Submission to the Medical Physics Journal for publication on Aug. 1999, 36 pages.
Kestin, L.L., et al., "Improving the Dosimetric Coverage of Interstitial High-Dose-Rate Breast Implants", Int. J. Radiat. Oncol. Biol. Phys., 2000, vol. 46, No. 1, pp. 35-43.
Kestin, L.L., et al., "Intensity Modulation to Improve Dose Uniformity with Tangential Breast Radiotherapy: Initial Clinical Experience" Int J. Radiat. Oncol. Biol. Phys., 2000, vol. 48, No. 5, pp. 1559-1568.
Kini, V.R., et al., "Use of Three-Dimensional Radiation Therapy Planning Tools and Intraoperative Ultrasound to Evaluate High Dose

(56) References Cited

OTHER PUBLICATIONS

Rate Prostate Brachytherapy Implants", Int. J. Radiat. Oncol. Biol. Phys., 1999, vol. 43, No. 3, pp. 571-578.

Kress, J., et al. "Patient position verification using CT images" Medical Physics, AIP, 26(6) 1999, 941-948.

Laughlin, J.S., et al., (writing chairs), "Evaluation of High Energy Photon External Beam Treatment Planning: Project Summary", Int. J. Rad. Oncol. Biol. Physics. 1991, vol. 21, pp. 3-8.

Martinez, A., et al., "Improvement in dose escalation using the process of adaptive radiation therapy combined with three dimensional conformal or Intensity modulated beams for prostate cancer", Int. J. Radiat. Oncol. Biol. Phys. 2001, vol. 50, No. 5, pp. 1226-1234.

Masterson, M.E., et al., "Inter-Institutional Experience in Verification of External Photon Dose Calculations", Int. J. Rad. Oncol. Biol. Physics, 1991, vol. 21, pp. 37-58.

Michalski, J., et al., "An Evaluation of Two Methods of Anatomical Alignment of Radiotherapy Portal Images", Int. J. Radiat. Oncol. Biol. Phys., 1993; vol. 27. No. 5, pp. 1199-1206.

Michalski, J.M., et al., "Prospective Clinical Evaluation of an Electronic Portal Imaging Device", Int. J. Radiat. Oncol. Biol. Phys., 1996, vol. 34, No. 4, pp. 943-951.

Michalski, J.M., et al., "The Use of On-Line Image Verification to Estimate the Variation in Radiation Therapy Dose Delivery", Int. J. Radiat. Oncol. Biol. Phys., 1993, vol. 27, No. 3, pp. 707-716.

Milliken, B.D., et al., "Verification of the Omni Wedge Technique", Med. Phys. Aug. 1998, vol. 25, No. 8, pp. 1419-1423.

Mohan, R. (writing chair), "Three-Dimensional Dose Calculations for Radiation Treatment Planning", Int. J. Rad. Oncol. Biol. Physics, May 15, 1991; vol. 21, No. 1, pp. 25-36.

Oldham, M., et al., "Practical aspects of in situ 160(y,n)150 activation using a conventional medical accelerator for the purpose of perfusion imaging", Med. Phys. Aug. 2001; vol. 28, No. 8, pp. 1669-1678.

Perera, H., et al., "Rapid Two-Dimensional Dose measurement in Brachytherapy Using Plastic Scintillator Sheet: Linearity, Signal-to-Noise Ratio, and Energy Response Characteristics.", Int. J. Radiat. Oncol. Biol. Phys., 1992, vol. 23, No. 5, pp. 1059-1069.

Pisani, L., et al., "Setup Error in Radiotherapy: On-line Correction Using Electronic Kilovoltage and Megavoltage Radiographs", Int. J. Radiat. Oncol. Biol. Phys., 2000, vol. 47, No. 3, pp. 825-839.

Purdy, J.A., et al., "State of the Art High Energy Photon Treatment Planning", Front Radiat. Ther. Oncol., 1987, vol. 21, pp. 4-24.

Schmidt, T.G. et al., A Prototype Table-Top Inverse-Geometry Volumetric CT Images; Med. Phys. vol. 33, No. 6 (Jun. 2006) pp. 1867-1878.

Sharpe, M.B., et al., "Compensation of X-Ray Beam Penumbra in Conformal Radiotherapy", Med. Phys., Aug. 2000, vol. 27, No. 8, pp. 1739-1745.

Sharpe, M.B., et al., "Monitor Unit Settings for Intensity Modulated Beams Delivered Using a Step-and-Shoot Approach", Med. Phys., Dec. 2000, vol. 27, No. 12, pp. 2719-2725.

Shikhaliev, P.M., et al., Photon Counting Computed Tomography: Concept and Initial Results; Med. Phys., vol. 32, No. 2, Feb. 2005, one page.

Shiu, A.S., et al., "Verification Data for Electron Beam Dose Algorithms", Med. Phys., May/Jun. 1992, vol. 19, No. 3, pp. 623-636.

Siewerdsen, et al., "Cone-Beam Computed Tomography with a Flat-Panel Imager: Effects of Image Lag," Med. Phys., vol. 26, No. 12, Dec. 1999, pp. 2635-2647.

Siewerdsen, et al., "Cone-Beam CT with a Flat-Panel Imager: Noise Consideration for Fully 3-D Computed Tomography," SPIE Physics of Medical Imaging, vol. 3336, Feb. 2000, pp. 546-554.

Siewerdsen, et al., "Optimization of X-Ray Imaging Geometry (with Specific Application to Flat-Panel Cone-Beam Computed Tomography)," Non-Final Version of Manuscript to be published in Med. Phys., vol. 27, No. 8, Aug. 2000, pp. 1-12.

Siewerdsen, J.H., et al., "A Ghost Story: Spatio-Temporal Response Characteristics of an Indirect-Detection Flat-Panel Imager", Med. Phys., Aug. 1999, vol. 26, No. 8, pp. 1624-1641.

Siewerdsen, J.H., et al., "Signal, Noise Power Spectrum, and Detective Quantum Efficiency of Indirect-Detection Flat-Panel Panel Imagers for Diagnostic Radiology", Med. Phys., May 1998, vol. 25, No. 5, pp. 614-628.

Siewerdsen, J.H., et al., "Cone-Beam Computed Tomography with a Flat-Panel Imager: Magnitude and Effects of X-Ray Scatter", Med. Phys., Feb. 2001, vol. 28, No. 2, pp. 220-231.

Siewerdsen, J.H., et al., "Empirical and Theoretical Investigation of the Noise Performance of Indirect Detection, Active Matrix Flat-Panel Imagers (AMFPIs) for Diagnostic Radiology", Med. Phys., Jan. 1997, vol. 24, No. 1, pp. 71-89.

Siewerdsen, J.H., et al., "Optimization of X-Ray Imaging Geometry (with Specific Application to Flat-Panel Cone-Beam Computed Tomography)", Med. Phys., Aug. 2000, vol. 27, No. 8, pp. 1903-1914.

Sontag, M.R. and Purdy, J.A. (writing chairs), "State of the Art of External Photon Beam Radiation Treatment Planning", Int. J. Rad. Oncol. Biol. Physics. 1991, vol. 21 No. 1, pp. 9-23.

Stromberg, J.S., et al., "Active Breathing Control (ABC) for Hodgkin's Disease: Reduction in Normal Tissue Irradiation with Deep Inspiration and Implications for Treatment", Int. J. Radiat. Oncol. Biol. Phys. 2000, vol. 48, No. 3, pp. 797-806.

Teicher, B.A., et al., "Allosteric Effectors of Hemoglobin as Modulators of Chemotherapy and Radiation Therapy In Vitro and In Vivo", Cancer Chemother. Pharmacol., 1998, vol. 42, pp. 24-30.

Tepper, J.E. and Shank, B. (writing Chairs), "Three-Dimensional Display in Planning Radiation Therapy: A Clinical Perspective", Int. J. Rad. Oncol. Biol. Physics. 1991, vol. 21, No. 1, pp. 79-89.

Urie, M.M., et al., "The Role of Uncertainty Analysis in Treatment Planning", Int. J. Radiat. Oncol. Biol. Phys., 1991, vol. 21, No. 1, pp. 91-107.

Vicini, F.A., et al., "Low-Dose-Rate Brachytherapy as the Sole Radiation Modality in the Management of Patients with Early-Stage Breast Cancer Treated with Breast-Concerving Therapy: Preliminary Results of a Pilot Trial", Int. J. Radiat. Oncol. Biol. Phys., 1997, vol. 38, No. 2, pp. 301-310.

Vicini, F.A., et al., "Dose-Volume Analysis for Quality Assurance of Interstitial Brachytherapy for Breast Cancer", Int. J. Radiat. Oncol. Biol. Phys., 1999, vol. 45, No. 3, pp. 803-810.

Vicini, F.A., et al., "Implementation of a 3D-Virtual Brachytherapy in the Management of Breast Cancer: a Description of a New Method of Interstitital Brachytherapy", Int. J. Radiat. Oncol. Biol. Phys., 1998, vol. 40, No. 3, pp. 629-635.

Webb, S., et al., Abstrct of Monte Carlo Modelling of the Performance of a Rotating Slit-collimator for Improved Planar Gamma-Camera Imaging; Phys. Med. Biol., vol. 37, No. 5, May 1992, one page.

Williamson, J.F., et al., "One-Dimensional Scatter-Subtraction Method for Brachytherapy Calculation Near Bounded Heterogeneities", Med. Phys., Jan./Feb. 1993, vol. 20, No. 1, pp. 233-244.

Wong, J.K., et al., "Conservative Management of Osteoradionecrosis", Oral Surg. Oral Med. Pahol. Oral Pathol., Jul. 1997, vol. 84, No. 1, pp. 16-21.

Wong, J.W., (writing chair), "Role of Inhomogeneity Corrections in 3D Photon Treatment Planning", Int. J. Rad. Oncol. Biol. Physics. 1991, vol. 21, No. 1, pp. 59-69.

Wong, J.W., et al., "Development of a Second-Generation Fiber-Optic On-Line Image Verification System", Int. J. Radiat. Oncol. Biol. Phys., 1993, vol. 26, No. 2, pp. 311-320.

Wong, J.W., et al., "Effect of Small Inhomogeneities on Dose in a Cobalt-60 Beam", Med. Phys., Nov./Dec. 1981, vol. 8, No. 6, pp. 783-791.

Wong, J.W., et al., "On Methods of Inhomogeneity Corrections for Photon Transport", Med. Phys., Sep./Oct. 1990, vol. 17, No. 5, pp. 807-814.

Wong, J.W., et al., "On-Line Image Verification in Radiation Therapy: An Early USA Experience", Med. Prog. Through Technol., 1993, vol. 19, pp. 43-54.

Wong, J.W., et al., "On-Line Radiotherapy Imaging with an Array of Fiber-Optic Image Reducers", Int. J. Radiat. Oncol. Biol. Phys., Jun. 1990, vol. 18, No. 6, pp. 1477-1484.

(56) References Cited

OTHER PUBLICATIONS

Wong, J.W., et al., "Portal Dose Images. I: Quantitative Treatment Plan Verification", Int. J. Radiat. Oncol.Biol.Phys., Jun. 1990, vol. 18, No. 6, pp. 1455-1463.

Wong, J.W., et al., "Reconsideration of the Power-Law (Batho) Equation for Inhomogeneity Corrections", Med. Phys., Jul./Aug. 1982, vol. 9, No. 4, pp. 521-530.

Wong, J.W., et al., "Second Scatter Contribution to Dose in Cobalt-60 Beam" Med. Phys., Nov./Dec. 1981, vol. 8, No. 6, pp. 775-782.

Wong, J.W., et al., "The Cumulative Verification Image Analysis Tool for Offline Evaluation of Portal Images", Int. J. Radiat. Oncol.Biol. Phys., 1995, vol. 33, No. 5, pp. 1301-1310.

Wong, J.W., et al., "The Use of Active Breathing Control (ABC) to Reduce Margin for Breathing Motion", Int. J. Radiat. Oncol. Biol. Phys., 1999, vol. 44, No. 4, pp. 911-919.

Wong, J.W., et al., "Treatment Verifications and Patient Dose Estimations Using Portal Dose Imaging" Radiotherapy System Research (Japan). 1988; vol. 5, No. 3, pp. 213-225.

Wong, J.W., et al.; "A New Approach to CT Pixel-Based Photon Dose Calculations in Heterogeneous Media", Med. Phys., Mar./Apr. 1983, vol. 10, No. 2, pp. 199-208.

Wu, Y., et al., "Implementing multiple static field delivery for intensity modulated beams", Med. Phys., Nov. 2001, vol. 28, No. 11, pp. 2188-2197.

Xu, Xiaochao, et al., "A tetrahedron beam computed tomography benchtop system with a multiple pixel field emission x-ray tube," Med. Phys., vol. 3, No. 10, Oct. 2011, pp. 5500-5508.

Yan, D., et al., "Adaptive Modification of Treatment Planning to Minimize the Deleterious effects of Treatment Setup Errors", Int. J. Radiat. Oncol. Biol. Phys., 1997, vol. 38, No. 1, pp. 197-206.

Yan, D., et al., "The influence of interpatient and intrapatient rectum variation on external beam treatment of prostate cancer", Int. J. Radiat. Oncol. Biol. Phys. 2001, vol. 51, No. 4, pp. 1111-1119.

Ping, X.G., et al., "Poital Dose Images. II: Patient Dose Estimation", Int. J. Radiat. Oncol. Biol. Phys., Jun. 1990, vol. 18, No. 6, pp. 1465-1475.

Yu, C.X., et al., "Photon Dose Perturbations Due to Small Inhomogeneities", Med. Phys., Jan./Feb. 1987, vol. 14, No. 1, pp. 78-83.

Yu, C.X., et al., "Photon Dose Calculation Incorporating Explicit Electron Transport", Med. Phys., Jul. 1995, vol. 22, No. 7, pp. 1157-1165.

Yu, C.X., et al., "A Method for Implementing Dynamic Photon Beam Intensity Modulation Using Independent Jaws and a Multileaf Collimator", Phys. Med. Biol., 1995, vol. 40, pp. 769-787.

Yu, C.X., et al., "A Multiray Model for Calculating Electron Pencil Beam Distribution", Med. Phys., Sep./Oct. 1988, vol. 15, No. 5, pp. 662-671.

Zeng, G.L., et al., Image Reconstruction Algorithm for a SPECT System with a Convergent Rotating Slat Collimator, IEEE Transactions on Nuclear Science, vol. 51, No. 1, Feb. 2004, pp. 142-148.

Zhang, Tiezhi, et al., Tetrahedron beam computed tomography (TBCT): a new design of volumetric CT system; Phys. Med. Biol., vol. 54, 2009, pp. 3365-3378.

Zhang, J., et al., A multi-beam X-ray Imaging System Based on Carbon Nanotube Field Emitters; Medical Imaging 2006; Physics of Medical Imaging Proceedings of SPIE; vol. 6142 (2006), eight pages.

International Search Report for PCT/US2007/012607, dated Apr. 11, 2008, one page.

Lucas, "Analysis of surface dose variation in CT procedures." The British Journal of Radiology, 74 (2001), 1128-1136.

Nakagawa, K. et al., "Development of a megavoltage ct scanner using linear accelerator treatment beam", Journal of JASTRO, vol. 3, No. 4, pp. 265-276, 1991, Japanese Society for Therapeutic Radiology and Oncology.

Shirato, H., "Real-time tumor tracking radiotherapy and stereotactic irradiation", Monthly New Medical Care, vol. 26, No. 12, pp. 61-63, 1999, ME Co., Ltd.

Vicini F et al. "NSABP/RTOG 0413: A randomized phase III study of conventional whole breast irradiation versus partial breast irradiation for women with Stage 0, I, or II breast cancer".

Hepel, Jaroslaw T. et al. "Toxicity of three-dimensional conformal radiotherapy for accelerated partial breast irradiation" Int. J. Radiat. Oncol. Biol. Phys., vol. 75, No. 5, 2009, pp. 1290-1296.

Jagsi Reshma et al. "Unacceptable cosmesis in a protocol investigating intensity modulated radiotherapy with active breathing control for accelerated partial breast irradiation" Int. J. Radiat. Oncol. Biol. Phys. Vo. 76, No. 1, 2009, pp. 71-78.

Livi, Lorenzo et al. "Accelerated partial breast irradiation with IMRT: new technical approach and interim analysis of acute toxicity in a phase III randomized clinical trial" Int. J. Radiat. Oncol. Biol. Phys. vol. 77, No. 2, 2010, pp. 509-515.

Smith, Benjamin D., et al., "Accelerated partial breast irradiation consensus statement from the american society for radiation oncology (ASTRO)," Int. J. Radiat. Oncol. Biol. Phys., vol. 74, No. 4, 2009, pp. 987-1001.

Veronesi, Umberto, et al., "Twenty year follow-up of a randomized study comparing breast-conserving surgery with radical mastectomy for early breast cancer," N. Engl. J. Med., vol. 347, No. 16, Oct. 17, 2002, pp. 1227-1232.

Jain, Anudh K., et al., "Does three-dimensional external beam partial breast irradiation spare lung tissue compared with standard whole breast irradiation?" Int. J. Radiat. Oncol. Biol, Phys., vol. 75, No. 1, 2009, pp. 82-88.

Recht, Abram, et al., "Lung dose-volume parameters and the risk of pneumonitis for patients treated with accelerated partial-breast irradiation using three-dimensional conformal radiotherapy," J. Clin. Oncol., vol. 27, No. 24, Aug. 20, 2009, pp. 3887-3893.

Low, Jennifer A,, et al., "Long-term follow-up for locally advanced and inflammatory breast cancer patients treated with multimodality therapy," J. Clin. Oncol., vol. 22, No. 20, Oct. 15, 2004, pp. 4067-4074.

Romond, Edward H., et al., "Trastuzumab plus adjuvant chemotherapy for operable HER2- positive breast cancer," N. Engl. J. Med., vol. 353, No. 16, Oct. 20, 2005, pp. 1673-1684.

Piccart-Gebhart, Martine J., et al., "Trastuzumab after adjuvant chemotherapy in HER2-positive breast cancer," N. Engl. J. Med., vol. 353, No. 16, Oct. 20, 2005, pp. 1659-1672.

Berrington de Gonzalez, A., et al., "Second solid cancers after radiotherapy for breast cancer in SEER cancer registries," Br. J. Cancer 2009, vol. 102, No. 1, Jan. 5, 2010, pp. 220-226.

Stovall, Marilyn, et al., "Dose to the contralateral breast from radiotherapy and risk of second primary breast cancer in the WECARE study," Int. J. Radiat. Oncol. Biol. Phys., vol. 72, No. 4, 2008, pp. 1021-1030.

Kozak, Kevin R, et al., "Dosimetric comparison of two different three-dimensional conformal external beam accelerated partial breast irradiation techniques," Int. J. Radiat. Oncol. Biol. Phys., vol. 65, No. 2, 2006, pp. 340-346.

Rusthoven, Kyle E., et al., "Accelerated partial-breast intensity-modulated radiotherapy results in improved dose distribution when compared with three-dimensional treatment-planning techniques," Int. J. Radiat. Oncol. Biol. Phys., vol. 70, No. 1, 2008, pp. 296-302.

Moran, Jean M., et al., "Accelerated partial breast irradiation: what is dosimetric effect of advanced technology approaches?," Int. J. Radiat. Oncol. Biol. Phys., vol. 75, No. 1, 2009, pp. 294-301.

Wernicke, A.G., et al., "External beam partial breast irradiation following breast-conserving surgery: preliminary results of cosmetic outcome of NYU 00-23," Int. J. Radiat. Oncol. Biol. Phys. vol. 66, No. 3, Supplement, 2006, p. S32.

Formenti, Silvia C., et al., "Prone accelerated partial breast irradiation after breast-conserving surgery: preliminary clinical results and dose-volume histogram analysis," Int. J. Radiat. Oncol. Biol. Phys., vol. 60, No. 2, 2004, pp. 493-504.

Kozak, Kevin R., et al., "Dosimetric comparison of proton and photon three-dimensional, conformal, external beam accelerated partial breast irradiation techniques," Int. J. Radiat. Oncol. Biol. Phys., vol. 65, No. 5, 2006, pp. 1572-1578.

Yu CX., "Intensity-modulated arc therapy with dynamic multileaf collimation: an alternative to tomotherapy," Phys. Med. Biol., vol. 40, 1995, pp. 1435-1449.

(56) References Cited

OTHER PUBLICATIONS

Yu, Cedric X., et al., "Clinical implementation of intensity-modulated arc therapy," Int. J. Radiat. Oncol. Biol. Phys.. vol. 53, No. 2, 2002, pp. 453-463.

Burgess, L., et al., "Partial Brain VMAT Planning Using Simultaneous Couch and Gantry Arcs," Int. L. Radiation Oncology Biol. Phys., vol. 78, Issue 3, Supplement 1, Nov. 1, 2010, pp. S818-S819.

Otto K., "Volumetric modulated arc therapy: IMRT in a single gantry arc," Med. Phys., vol. 35, 2008, pp. 310-317.

Palma, David, et al., „Volumetric modulated arc therapy for delivery of prostate radiotherapy: comparison with intensity-modulated radiotherapy and three-dimensional conformal radiotherapy, Int. J. Radiat. Oncol. Biol. Phys., vol. 72, No. 4, 2008, pp. 996-1001.

Duthoy, W., et al., "Clinical implementation of intensity-modulated arc therapy (IMAT) for rectal cancer," Int. J. Radiat. Oncol. Biol. Phys., vol. 60, No. 3, 2004, pp. 794-806.

Lagerwaard FJ., et al., "Whole-brain radiotherapy with simultaneous integrated boost to multiple brain metastases using volumetric modulated arc therapy," Int. J. Radiat. Oncol. Biol. Phys., vol. 75, No. 1, 2009, pp. 253-259.

Popescu CC., et al., "Volumetric modulated arc therapy improves dosimetry and reduces treatment time compared to conventional intensity-modulated radiotherapy for locoregional radiotherapy of left-sided breast cancer and internal mammary nodes," Int J Radiat Oncol Biol Phys, vol. 76, No. 1, 2009, pp. 287-295.

Clarke M., et al., "Effects of radiotherapy and of differences in the extent of surgery for early breast cancer on local recurrence and 15-year survival: An overview of the randomised trials," Lancet, vol. 366, 2005, pp. 2087-2106.

Paszat, Lawrence F., et al., "Mortality from myocardial infarction following postlumpectomy radiotherapy for breast cancer. A population-based study in Ontario, Canada," Int J Radiat Oncol Biol Phys, vol. 43, No. 4, 1999, pp. 755-762.

Baglan, Kathy L. et al., "Accelerated partial breast irradiation using 3D conformal radiation therapy (3D-CRT)," Int J Radiat Oncol Biol Phys, vol. 55, No. 2, 2003, pp. 302-311.

Pignol, Jean-Philippe, et al., "A multicenter randomized trial of breast intensity-modulated radiation therapy to reduce acute radiation dermatitis," J Clin Oncol, vol. 26, No. 13, May 1, 2008, pp. 2085-2092.

Reeder, Reed, et al., "Predictors for clinical outcomes after accelerated partial breast intensity-modulated radiotherapy," Int J Radiat Oncol Biol Phys, vol. 74. No. 1, 2009, pp. 92-97.

Hall, Eric J., et al., "Radiation-induced second cancers: The impact of 3D-CRT and IMRT," Int J Radiat Oncol Biol Phys, vol. 56, No. 1, 2003, pp. 83-88.

Shaitelman, Simona F., et al., "Continuous Arc Rotation of the Couch Therapy for the Delivery of Accelerated Partial Breast Irradiation: A Treatment Planning Analysis," Int. J. Radiation Oncology Biol. Phys., vol. 80, No. 3, 2011, pp. 771-778.

Takahashi, S., "Conformation Radiotherapy. Rotation Techniques as Applied to Radiography and Radiotherapy of Cancer," Acta Radiol, Diagn (Stockh), Suppl 242:1+, 1965, pp. 11-140.

Kim, L., et al., "Volumetric Modulated Arc Therapy Using a Rotating Couch: An Accelerated Partial Breast Irradiation Planning Study," Int. L. Radiation Oncology Biol. Phys., vol. 75, Issue 3, Supplement 1, Nov. 1, 2009, pp. S732-S733.

Yasuda, Takami "State of the Art and Future Possibility of Image Applications in Medicine"; Institute of Television Engineers of Japan (ITE), vol. 16(47), Jul. 23, 1992 with English Abstract included.

Inamura, Seiya "Future for Digital X-Ray", Monthly New Medical Care, vol. 26, No. 4, pp. 72-78, published Apr. 1, 1999 with translation of relevant portions of Abstract.

Japanese Office Action dated Jan. 15, 2015 in JP Application No. 2001-559337.

International Search Report and Written Opinion for International Application No. PCT/US2011/000006, mailed Mar. 1, 2011.

International Search Report and Written Opinion for International Application No. PCT/US2007/008996, mailed Mar. 4, 2008, three pages.

\* cited by examiner

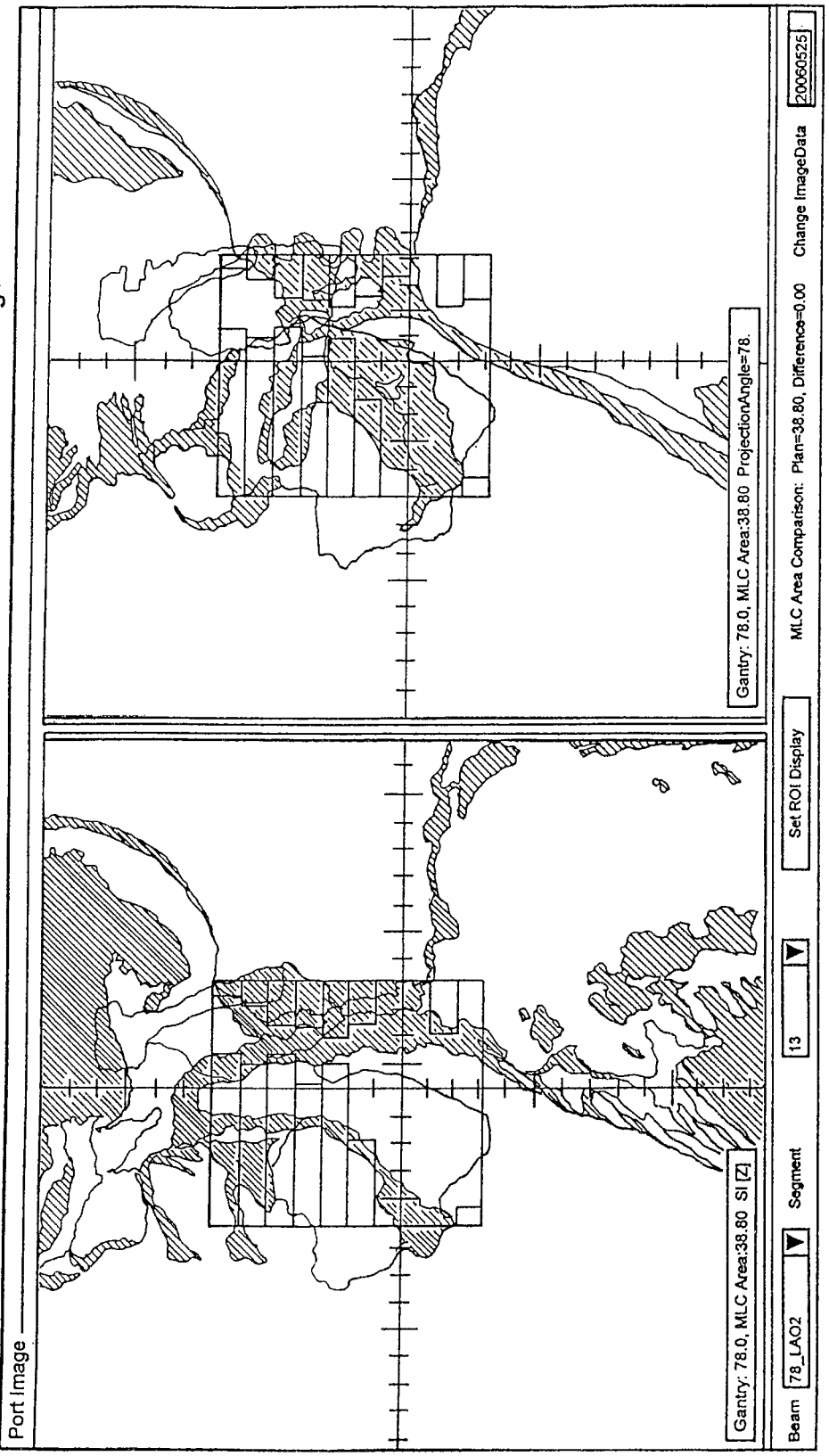

REAL-TIME, ON-LINE AND OFFLINE TREATMENT DOSE TRACKING AND FEEDBACK PROCESS FOR VOLUMETRIC IMAGE GUIDED ADAPTIVE RADIOTHERAPY Applicants claim, under 35 U.S.C. §119(e), the benefit of priority of 1) the filing date of May 25, 2006, of U.S. Provisional Patent Application Ser. No. 60/808,343, filed on the aforementioned date and 2) the filing date of Jan. 18, 2007, of U.S. Provisional Patent Application Ser. No. 60/881,092, filed on the aforementioned date, the entire contents of each of which are incorporated herein by reference.

BACKGROUND OF THE INVENTION

1. Field of the Invention

The present invention relates generally to image guided radiotherapy, and in particular, the invention relates to volumetric image guided adaptive radiotherapy.

2. Discussion of the Related Art

Presently, online treatment dose construction and estimation include portal ex-dose reconstruction to reconstruct treatment dose on a conventional linear accelerator. Specifically, the exit dose is measured using an MV portal imager to estimate treatment dose in the patient. However, this method has not been employed for patient treatment dose construction, since the dose reconstruction method lacks patient anatomic information during the treatment, and the scattered exit dose is difficult to calibrate properly.

In the past, a single pre-treatment computed tomography scan has been used to design a patient treatment plan for radiotherapy. Use of such a single pre-treatment scan can lead to a large planning target margin and uncertainty in normal tissue dose due to patient variations, such as organ movement, shrinkage and deformation, that can occur from the start of a treatment session to the end of the treatment session.

BRIEF SUMMARY OF THE INVENTION

One aspect of the present invention regards a system for radiotherapy that includes an imaging system that generates volumetric image data of an area of interest of an object and a radiation source that emits a therapeutic radiation beam towards the area of interest of the object in accordance with a reference plan. The system for radiotherapy further includes a processing system that receives and evaluates the volumetric image data and at least one parameter of the therapeutic radiation beam to provide a real-time, on-line or off-line evaluation and on-line or off-line modification of the reference plan.

A second aspect of the present invention regards a method of treating an object with radiation that includes generating volumetric image data of an area of interest of an object and emitting a therapeutic radiation beam towards the area of interest of the object in accordance with a reference plan. The method further includes evaluating the volumetric image data and at least one parameter of the therapeutic radiation beam to provide a real-time, on-line or off-line evaluation and on-line or off-line modification of the reference plan.

A third aspect of the present invention regards a planning and control system for radiotherapy that includes a system that captures and evaluates parameters of a volumetric image of an area of interest of an object and a therapeutic radiation beam directed towards the area of interest of the object in accordance with a reference plan so as to provide a real-time, on-line or off-line evaluation and on-line or off-line modification of the reference plan. The system further includes a monitor that displays information based on one or more of the captured parameters of the volumetric image and the therapeutic radiation beam.

A fourth aspect of the present invention regards a method of planning and controlling a radiation therapy session, the method including capturing and evaluating parameters of a volumetric image of an area of interest of an object and a therapeutic radiation beam directed towards the area of interest of the object in accordance with a reference plan so as to provide a real-time, on-line or off-line evaluation and on-line or off-line modification of the reference plan. The method further including displaying information based on one or more of the captured parameters of the volumetric image and the therapeutic radiation beam.

A fifth aspect of the present invention regards a system for radiotherapy that includes a radiation source that is programmed to emit a therapeutic radiation beam towards an area of interest of an object in accordance with a reference plan during a real-time time period when the object is on-line. The system further includes an imaging system that generates on-line volumetric image data of the area of interest of the object during the real-time time period when the object is on-line, and off-line volumetric image data of the area of interest of the object during a non-real time off-line time period. The system further includes a processing system that receives and processes one or more of the on-line and off-line volumetric image data to alter the reference plan.

A sixth aspect of the present invention regards a method of treating an object with radiation that includes planning on emitting a therapeutic radiation beam towards an area of interest of an object in accordance with a reference plan during a real-time time period when the object is on-line. The method includes generating on-line volumetric image data of the area of interest of the object during the real-time time period when the object is on-line, and off-line volumetric image data of the area of interest of the object during a non-real time off-line time period. The method further includes altering the reference plan based on one or more of the on-line and off-line volumetric image data.

A seventh aspect of the present invention regards a method of forming a portal image, the method including forming a two-dimensional image of an object of interest and superimposing an image of a collimator element on the two-dimensional image. The image represents the position of the collimator element when a radiation therapy beam is to be directed towards the object of interest.

One or more aspects of the present invention provide the advantage of providing online and offline treatment dose reconstruction, and a treatment decision tool that provides real-time, on-line and off-line treatment evaluation and on-line or off-line modification of a reference plan.

Additional objects, advantages and features of the present invention will become apparent from the following description and the appended claims when taken in conjunction with the accompanying drawings.

BRIEF DESCRIPTION OF THE DRAWINGS

FIGS. 4a-b show a reference image and a kV portal image with a beam eye view of organs of interest:

PREFERRED EMBODIMENTS OF THE INVENTION

Figure 1:
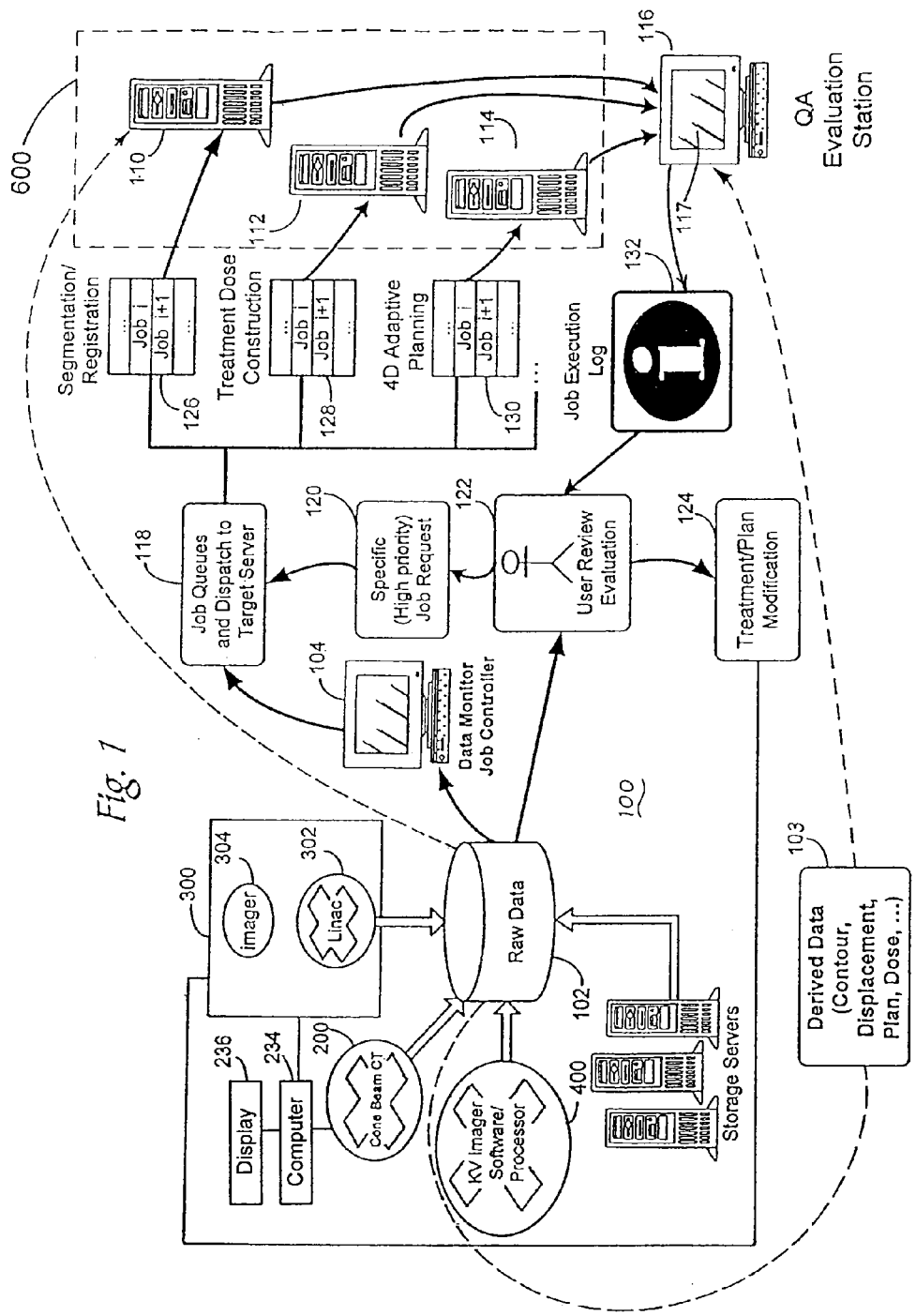
FIG. 1 schematically shows an embodiment of a radiation therapy system that employs a dose tracking and feedback process and a possible workflow for auto-construction, estimation and evaluation of cumulative treatment dose, and patient anatomy and dose feedback for adaptive planning optimization in accordance with the present invention.

In accordance with the present invention, a volumetric image guided adaptive radiotherapy system, such as cone-beam computerized tomography (CBCT) image guided adaptive radiotherapy (IGART) system 100, and a corresponding workflow sequence for auto-construction and evaluation of daily cumulative treatment dose are shown in FIGS. 1-7, wherein like elements are denoted by like numerals. As shown in FIG. 1, the CBCT IGART system 100 includes a number of major systems: 1) a three-dimensional volumetric imaging system, such as an x-ray cone-beam computed tomography system 200, 2) a megavoltage imaging system 300 that includes a radiation therapy source, such as a linear accelerator 302, and an imager 304, 3) a kV portal imager processor/software system 400 and 4) a treatment dose tracking and feedback system 600, each of which are discussed below.

Three-Dimensional Volumetric Imaging System

Mechanical operation of a cone-beam computed tomography system 200 is similar to that of a conventional computed tomography system, with the exception that an entire volumetric image is acquired through less than two rotations (preferably one rotation) of the source and detector. This is made possible by the use of a two-dimensional (2-D) detector, as opposed to the one-dimensional (1-D) detectors used in conventional computed tomography.

An example of a known cone-beam computed tomography imaging system is described in U.S. Pat. No. 6,842,502, the entire contents of which are incorporated herein by reference. The patent describes an embodiment of a cone-beam computed tomography imaging system that includes a kilovoltage x-ray tube and a flat panel imager having an array of amorphous silicon detectors. As a patient lies upon a treatment table, the x-ray tube and flat panel image rotate about the patient in unison so as to take a plurality of images as described previously.

Figure 2A:
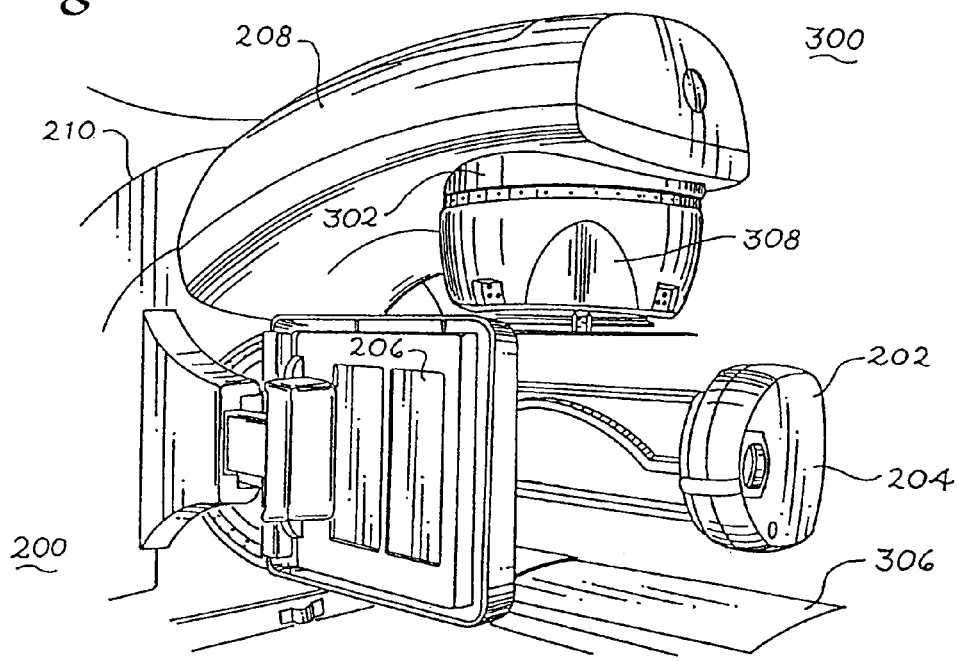
FIGS. 2a-c show various embodiments of onboard imaging systems and/or radiation therapy systems to be used with the radiation therapy system of FIG. 1 for performing dose tracking and feedback.
Figure 2B:
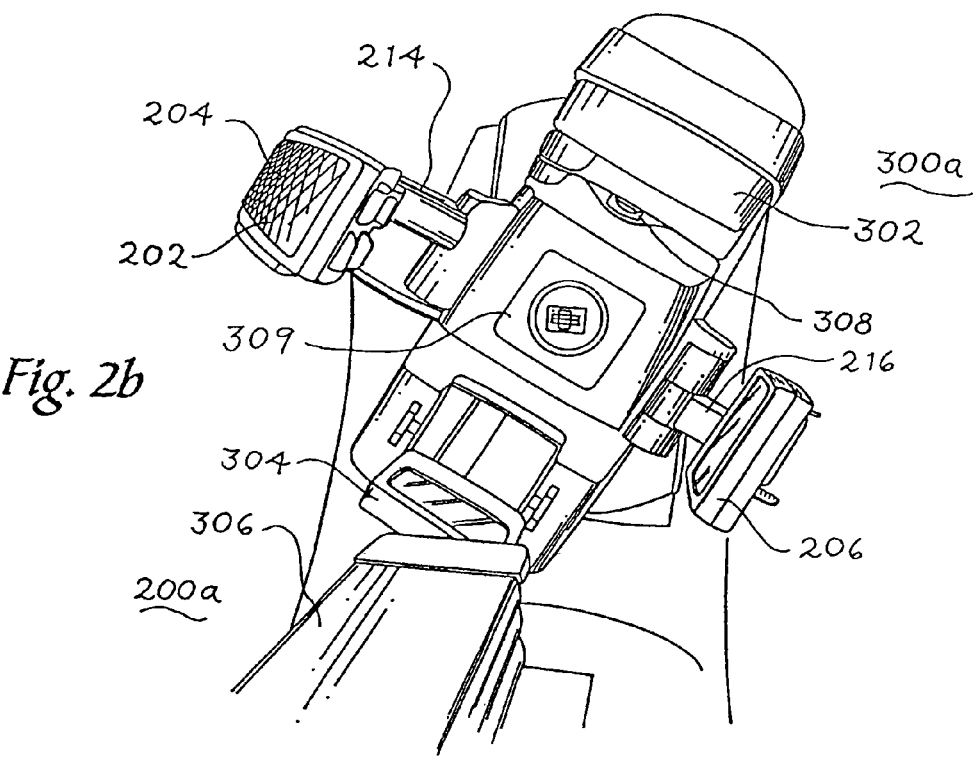
Figure 2C:
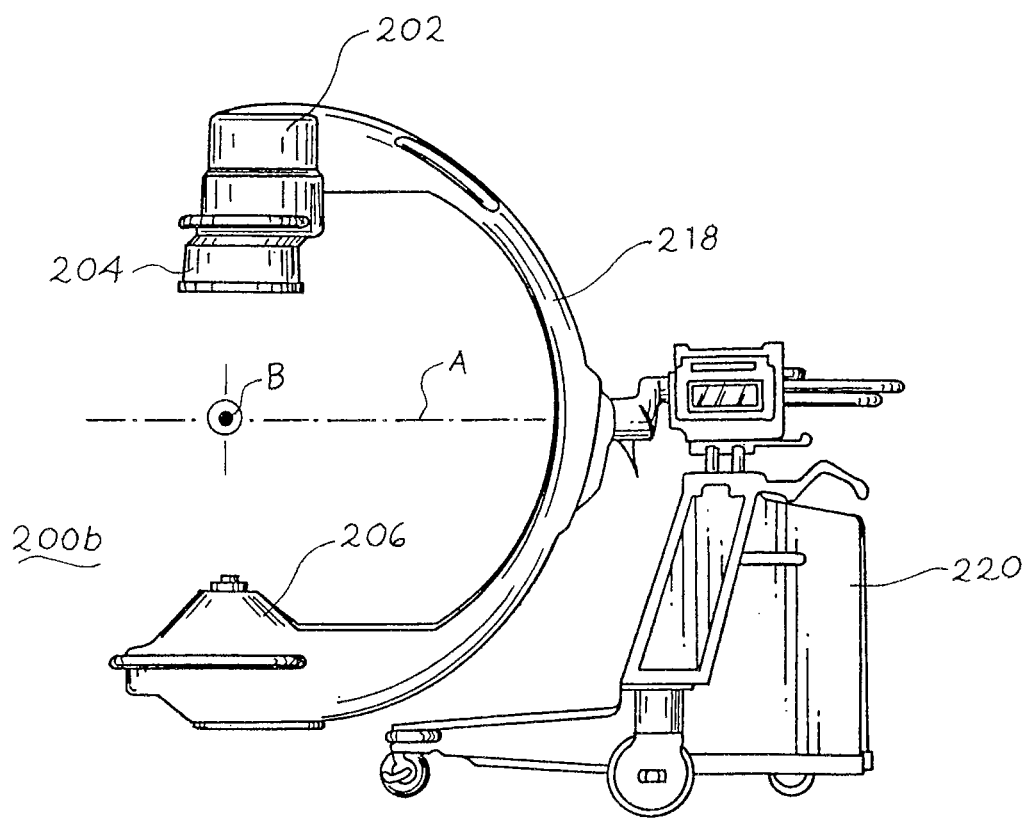

As shown in FIGS. 2a-c, various volumetric imaging systems to be used with the present invention are illustrated. While the discussion to follow will describe the cone-beam computed tomography system 200 and megavoltage portal imaging system 300 of FIG. 2a, the discussion will be equally applicable to the scanning slot cone-beam computed tomography and megavoltage portal imaging systems of FIGS. 2b-c. FIG. 2a shows an embodiment of a wall-mounted cone-beam computed tomography system 200 and megavoltage portal imaging system 300 that can be adapted to be used with the cone-beam computed tomography and megavoltage portal imaging system sold under the trade name Synergy by Elekta of Crawley, the United Kingdom. Such systems 200 and 300 are described in pending U.S. patent application Ser. No. 11/786,781, entitled "Scanning Slot Cone-Beam Computed Tomography and Scanning Focus Spot Cone-Beam Computed Tomography" and filed on Apr. 12, 2007, the entire contents of which are incorporated herein by reference.

The cone-beam computed tomography system 200 includes an x-ray source, such as x-ray tube 202, a rotary collimator 204 and a flat-panel imager/detector 206 mounted on a gantry 208. As shown in FIG. 2a, the flat-panel imager 206 can be mounted to the face of a flat, circular, rotatable drum 210 of the gantry 208 of a medical linear accelerator 302, where the x-ray beam produced by the x-ray tube 202 is approximately orthogonal to the treatment beam produced by the radiation therapy source 302. Note that an example of mounting an x-ray tube and an imager to a rotatable drum is described in U.S. Pat. No. 6,842,502, the entire contents of which are incorporated herein by reference.

Note that the detector 206 can be composed of a two-dimensional array of semiconductor sensors that may be each made of amorphous silicon ($\alpha$-Si:H) and thin-film transistors. The analog signal from each sensor is integrated and digitized. The digital values are transferred to the data storage server 102.

After the fan beams from collimator 204 traverse the width of a patient and impinge on the entire detector 206 in the manner described above, computer 234 of FIG. 1 instructs the drum 210 to rotate causing the x-ray source 202, the collimator 204 and the detector 206 rotate about the patient to another position so that the scanning process described above can be repeated and another two-dimensional projection is generated. The above rotation of the x-ray source 202, collimator 204 and detector 206 is continued until a sufficient number of two-dimensional images are acquired for forming a cone-beam computed tomography image. Less than two rotations should be needed for this purpose (it is envisioned that images formed from a rotation of less than 360° can be formed as well). The two-dimensional projections from each position are combined in the computer 234 to generate a three-dimensional image to be shown on display 236 of FIG. 1 in a manner similar to that of the cone-beam computed tomography systems described previously.

While the above described embodiment for the collimator 208 is rotary, a linear moving collimator can be used instead as described in pending U.S. patent application Ser. No. 11/786,781, entitled "Scanning Slot Cone-Beam Computed Tomography and Scanning Focus Spot Cone-Beam Computed Tomography" and filed on Apr. 12, 2007, the entire contents of which are incorporated herein by reference.

Radiation Therapy Source and Imager

As shown in FIG. 2a, (original) The system 300 includes a separate radiation therapy x-ray source, such as a linear source 302, and a detector/imager 304 that are separately mounted to the rotating drum 210. The source 302 operates at a power level higher than that of x-ray tube 202 so as to allow for treatment of a target volume in a patient lying on movable table 306 (movable in x, y and z-direction via computer 234 of FIG. 1). The linear source 302 generates a beam of x-rays or particles, such as photons, protons or electrons, which have an energy ranging from 4 MeV to 25 MeV.

As mentioned above, the particles are used to treat a specific area of interest of a patient, such as a tumor. Prior to arriving at the area of interest, the beam of particles is shaped to have a particular cross-sectional area via a multi-leaf collimator 308. The cross-sectional area is chosen so that the beam of particles interacts with the area of interest to be treated and not areas of the patient that are healthy. The radiation penetrating through the area of interest can be imaged via imager 304 in a well known manner.

Alternative Embodiments for Volumetric Imaging System and Radiation Source and Imager Another embodiment of a cone-beam computed tomography system 200a and megavoltage portal imaging system 300a is shown in FIG. 2b. In this embodiment, the systems 200a and 300a can be adapted to be used with the cone-beam computed tomography and megavoltage portal imaging system sold under the trade name Trilogy by Varian Medical Systems of Palo Alto, Calif. The system 200a includes an x-ray tube 202, a rotary collimator 204 and a flat-panel imager/detector 206 similar to those used in the embodiment of FIG. 2a. Unlike the system 200 of FIG. 2a mounted on a drum, the x-ray tube 202 and collimator 204 are mounted on an arm 214 pivotably mounted to a support 309 of the system 300a. Similarly, the flat panel imager 206 is mounted on an arm 216 mounted to the support 309.

As with the embodiment of FIG. 2a, the x-ray beam 212 produced by the x-ray tube 202 of FIG. 2b is approximately orthogonal to the treatment beam produced by the radiation therapy source 302. As shown in FIG. 2b, the system 300a includes a linear source 302 and detector 304 similar to those described previously with respect to FIG. 2a. Accordingly, the linear source 302 generates a beam of x-rays or particles, such as photons or electrons, which have an energy ranging from 4 MeV to 25 MeV so as to allow for treatment of a target volume in a patient lying on movable table 306 (movable in x, y and z-direction via computer 234 of FIG. 1). Unlike the system 300 of FIG. 2a mounted on a drum, the linear source 302 and the detector 304 are connected with support 309.

Another embodiment of a scanning slot cone-beam computed tomography system 200b is shown in FIG. 2c. In this embodiment, system 200b includes a kilo-voltage x-ray tube 202, a rotary collimator 204 and a flat-panel imager/detector 206 similar to those used in the embodiment of FIG. 2a. Unlike the system 200 of FIG. 2a mounted on a drum, the x-ray tube 202 and collimator 204 are mounted at one end of a C-arm 218 while the flat panel imager 206 is mounted at the other end of the C-arm 218. The C-arm 218 is mounted to a movable base 220 so that it can pivot about axes A and B shown in FIG. 2c.

Treatment Dose Tracking and Feedback System

As shown in FIG. 1, the treatment dose tracking and feedback system 600 includes a workstation or data server 110 that includes processors dedicated to perform a segmentation/registration process on a three-dimensional, volumetric image of a patient received from server 102 that was generated by cone-beam computed tomography system 200. The workstation 110 is able to identify and register each volume of image data within each volumetric image. Such identification and registration allows for the same volume of image data to be tracked in position from one therapy session to another therapy session.

The treatment dose tracking and feedback system 600 further includes a workstation or data server 112 that includes processors dedicated to perform a treatment dose construction process based on 1) the segmentation/registration process performed by workstation 110 and 2) parameters of the beam of radiation emitted from the source 302 as it impinges on the patient that are measured and stored in server 102, such as angular position, beam energy and cross-sectional shape of the beam, in accordance with the reference plan 502. Such parameters can be in the form of the angular position of the gantry 208, the angular orientation of the collimator 308, the positions of the leaves of the multi-leaf collimator 308, position of the table 306 and energy of the radiation beam. Once the position and shape of a subvolume of image data is known, the treatment dosage received by that very same subvolume can be determined/constructed based on the above mentioned parameters of the beam of radiation emitted from the source 302 as it impinges on the patient. Such a determination is made for each of the subvolumes of image data for each of the volumetric images generated by system 200.

The treatment dose tracking and feedback system 600 further includes a workstation or data server 114 that includes processors dedicated to perform a an adaptive planning process that can either 1) adjust the radiation therapy treatment for the particular day in a real-time manner based on off-line and on-line information or 2) adjust a radiation therapy treatment plan in a non-real-time manner based on off-line information. The adjustment is based on how the dose calculated by the workstation 112 differs from dose preferred by the treatment plan. Note that the term "real-time" refers to the time period when the radiation therapy source is activated and treating the patient. The term "on-line" regards when a patient is on the treatment table and "off-line" refers to when the patient is off the treatment table.

In summary, the treatment dose tracking and feedback system 600 can perform real time treatment dose construction and 4D adaptive planning based on volumetric image information and therapy beam parameters that are measured in a real time manner during a therapy session. The system 600 can also perform adaptive planning in a non-real-time manner as well. Such real time and non-real time processes will be discussed in more detail with respect to the process schematically shown in FIG. 7. Note that in an alternative embodiment, the workstations 110, 112 and 114 can be combined into a single workstation wherein the processes associated with workstations 110, 112 and 114 are performed by one or more processors. Note that the real time treatment dose construction determined by workstation 112 and the 4D adaptive planning determined by workstation 114 can be displayed on a monitor 117 of Quality Assurance (QA) evaluation station 116. Based on the information displayed on monitor 117, medical personnel can alter, if required, the calculated 4D adaptive plan so as to be within acceptable parameters. Thus, the QA evaluation station 116 acts as a way to ensure confidence in future real time changes made to the therapy session. In this scenario, the QA evaluation station 116 and the treatment dose tracking and feedback system 600 can be collectively thought of as a 4D planning and control system.

With the above description of the onboard cone-beam computed tomography system 200, megavoltage imaging and radiation therapy system 300, QA evaluation station 116 and the treatment dose tracking and feedback system 600 in mind, the operation of the CBCT IGART system 100 of FIG. 1 can be understood. In particular, the previously described online volumetric imaging information and real time therapy beam parameters are captured from systems 200, 300 and 400 and stored in data storage server 102. The volumetric imaging information and therapy beam parameters are then sent to data monitor job controller 104 that automatically assigns tasks, based on pre-designed treatment schedule and protocol, to each of the work stations 110, 112 and 114 and controls the accomplishment of such tasks. The tasks are stored in temporal job queues 118 for dispatching, based on clinical priorities, to each of the workstations 110, 112 and 114. The clinical priority can be reassigned from a clinical user's request 120 based on the treatment review and evaluation on the physician evaluation/decision making station 122. In addition, the station 122 also provides commands for treatment/plan modification decisions. The modification server 124 receives commands from the station 122 and modifies the ongoing treatment plan, beam or patient position on the system 300 based on the optimized adaptive plan created from the adaptive planning workstation 114.

As shown in FIG. 1, the raw data from server 102 is also sent to a workstation 110. The workstation 110 is dedicated to perform an autosegmentation/registration process on a three-dimensional, volumetric image of a patient generated by cone-beam computed tomography system 200. The raw data from server 102 is also sent to workstation 112 and workstation 114. Workstation 112 performs daily and cumulative treatment dose construction/evaluation from the raw data. Workstation 114 performs adaptive planning from the raw data. These three workstations 110, 112 and 114 perform their tasks automatically with order of their job queues 126, 128 and 130, respectively. The above described segmentation/registration, treatment dose construction/evaluation and adaptive planning will be described later with respect to the process schematically shown in FIG. 7.

As shown in FIG. 1, the segmentation/registration, treatment dose construction and adaptive planning information generated from workstations 110, 112 and 114 is sent to the QA evaluation station 116 which interacts with a clinical user to verify and modify, if necessary, the results from the above workstations 110, 112 and 114. The output from QA evaluation station 116 is then stored in derived data server 102. The output from QA evaluation station 116 is then stored in derived data server 103.

The QA station 116 provides an update execution status to job execution log server 132 that supplies information whether processing of information is presently occurring, whether processing is completed or whether an error has occurred. Whenever a task of treatment dose construction or adaptive planning modification is completed by workstations 112 and 114, respectively, the evaluation station 116 provides treatment evaluation information which includes both the current treatment status and the completed treatment dose and outcome parameters estimated based on the patient and treatment data from previous treatments. The user at QA evaluation station 116 can then provide commands or a new clinical schedule to the high priority job request server 120 to either request new information or modify clinical treatment schedule. In addition, the user can also make decisions to execute a new adaptive plan or perform a treatment/patient position correction through the server 124.

The CBCT IGART system 100 performs a number of processes, including a kV portal imaging process via kV portal imaging processor/software 400 and a an image guided adapted radiation therapy process 500, both of which will be described below with respect to FIGS. 3-7.

Pre-Treatment Process

As an example of how the radiation therapy process proceeds, assume a patient who has undergone previous radiation therapy sessions at a clinic has another session scheduled for a particular day. The patient arrives at the clinic on the scheduled day and proceeds to the therapy room similar to that shown in FIG. 3a. The therapy room includes the cone-beam computed tomography system 200 and megavoltage portal imaging system 300 previously described with respect to FIG. 2a. The patient lies on the table 306 and is prepared for the on-line therapy session by the medical staff ("on-line" being defined as events and processes performed as the patient is positioned on the radiation therapy treatment table 306).

At this point of time, a reference treatment plan for applying therapeutic radiation to the patient has previously been determined for the patient based on the previous radiation therapy sessions. A reference treatment plan is designed before the treatment delivery based on the most likely planning volumetric image of the area of interest to be treated. The reference treatment plan contains patient setup position, therapy machine parameters and expected daily and cumulative doses to be applied to various areas of the patient. Such a reference plan specifies the area(s) of the patient to be exposed to radiation and the dosage the area(s) are to receive from the radiation source during a single session. Thus, the reference plan will include information regarding the beam angle/gantry position, beam energy and cross-sectional area of the beam formed by the multi-leaf collimator 308. Based on the reference plan, the patient is instructed per step 402 of a pre-treatment kV portal imaging process, to move to a particular position, such as on his or her side, that is optimal for applying radiation to the area of interest within the patient per the reference plan. While at the particular position, the previously mentioned pre-treatment kV portal imaging process employing kV processor/software 400 is performed prior to the radiation therapy session. The pre-treatment kV portal imaging process is schematically shown in FIGS. 3-6. In particular, the process includes forming a two-dimensional projection/radiographic image from the cone-beam computed tomographic image 404 of the patient prior to treatment, wherein the image 404 contains the area of interest while the patient is at the particular position on the table 306 per step 406 of the process. According to the reference plan, the radiation source 302 is to be moved to one or more positions to apply radiation at each position while the patient is at the particular position. At each position of the radiation source 302, the leaves of the multi-leaf collimator 308 are to be moved to form a desired outline for forming the radiation beam to a particular cross-sectional shape. The positions of the leaves at each position of the radiation source are determined, per step 408, as schematically represented by the multi-leaf outlines 410 of FIGS. 3a-b.

Figure 3A:
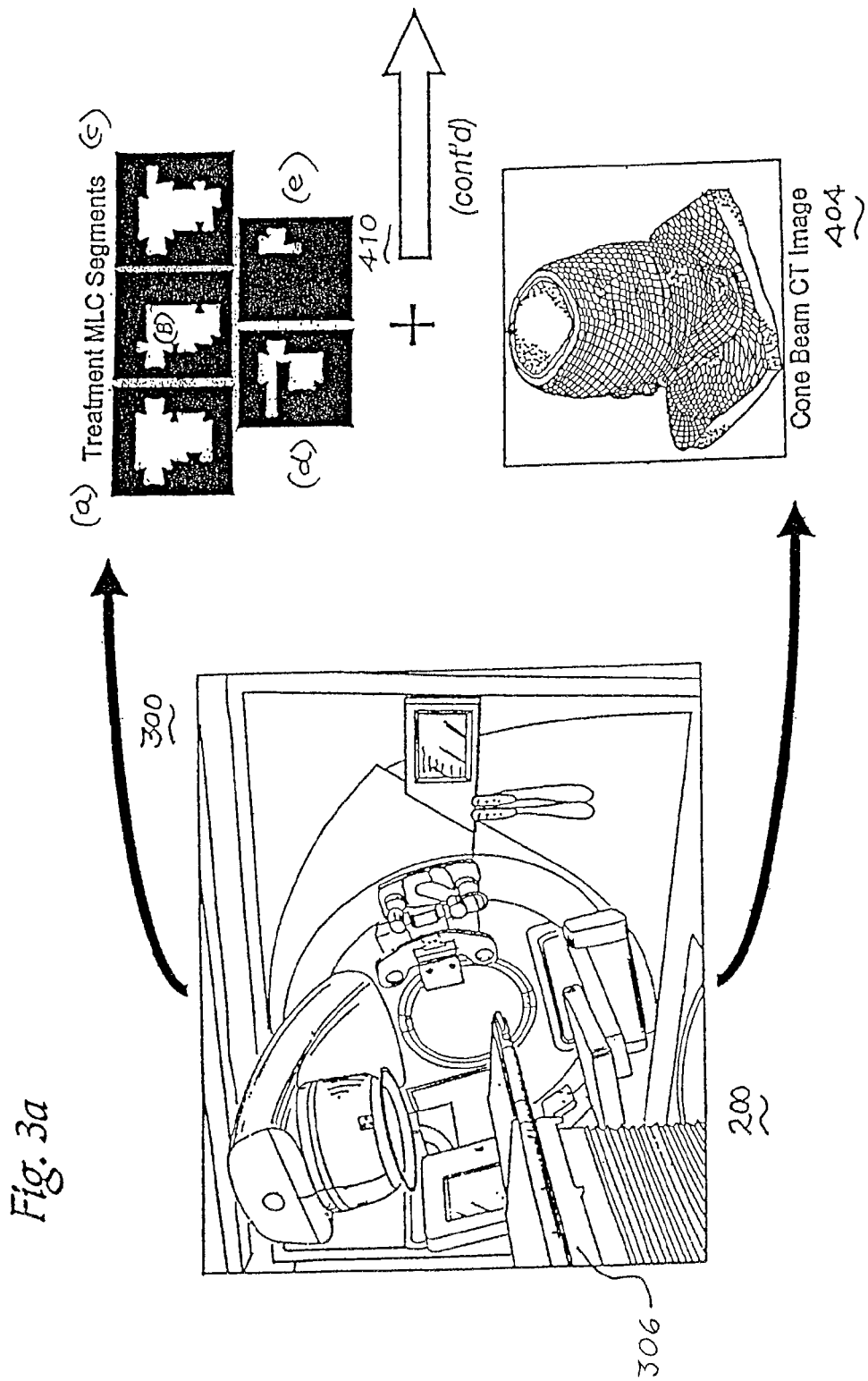
FIGS. 3a-b provides a visual representation of a possible process to form a kV portal image.
Figure 3B:
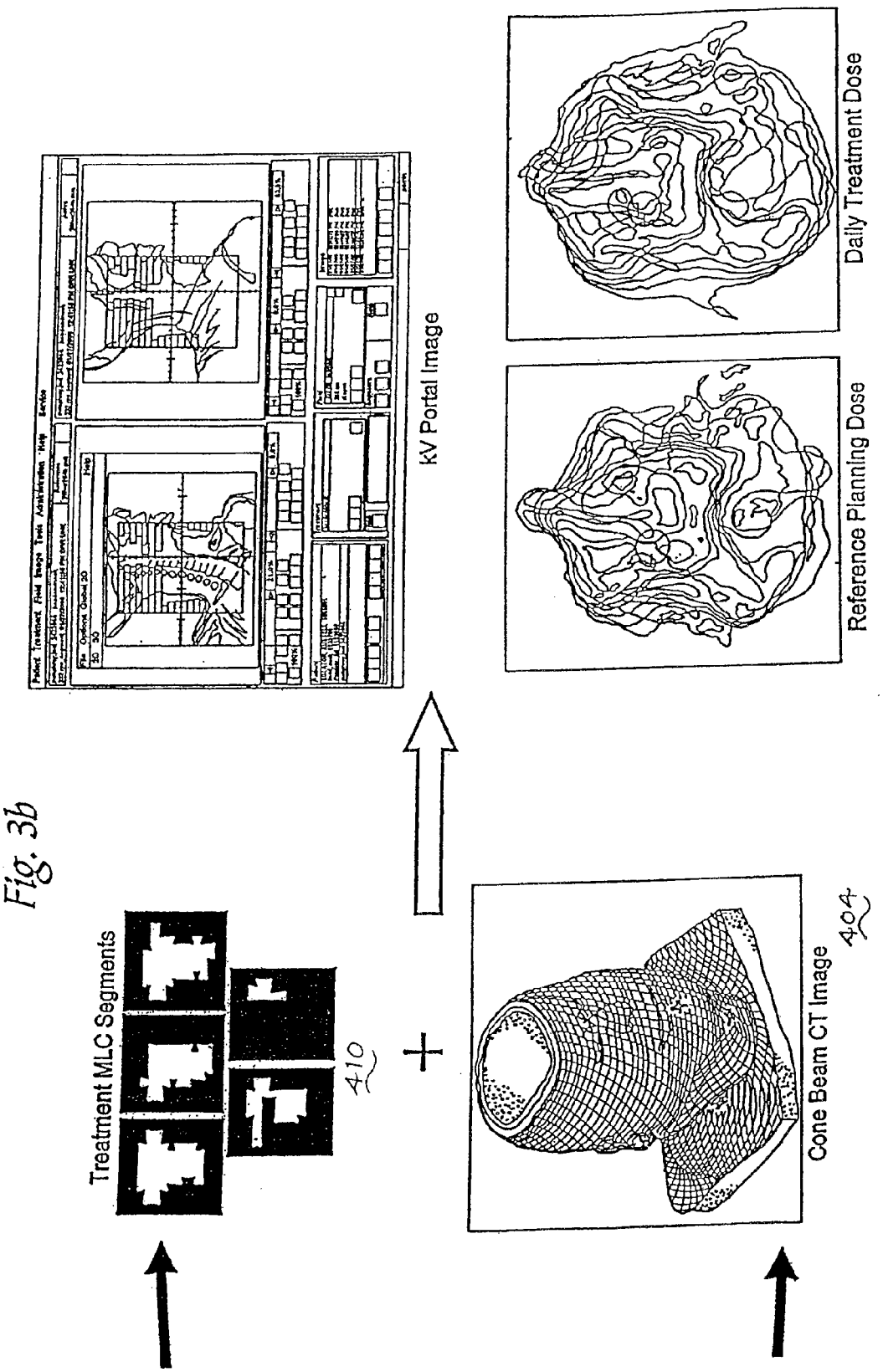
Figure 5:
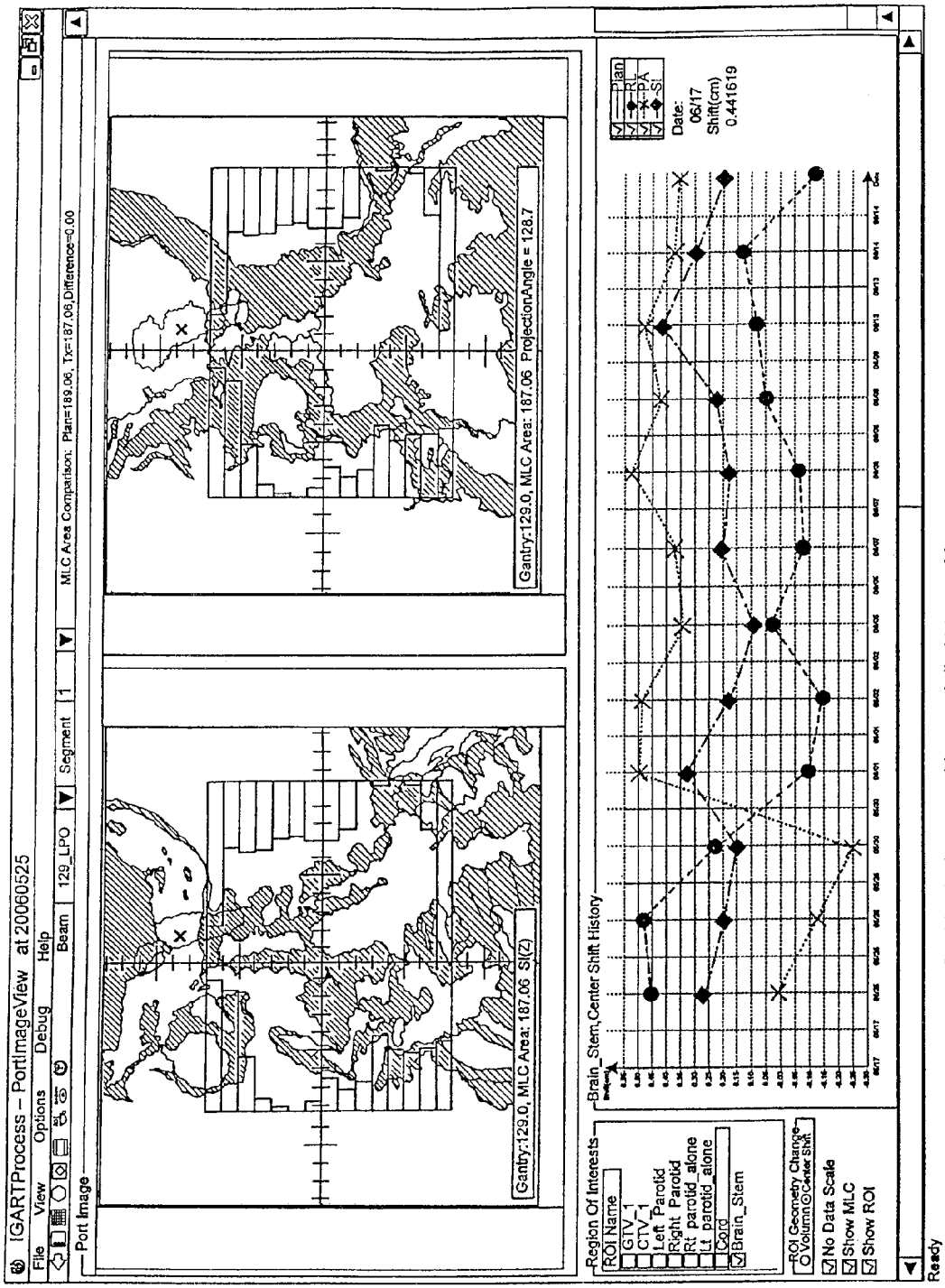
FIG. 5 shows a possible image on a quality assurance workstation that shows kV portal images with a position/volume tracking chart for a daily kV portal image.

The cone-beam computed tomographic image 404 of the area of interest while the patient is at the particular position and the positions of the leaves/outlines 410 are then stored and processed in a processor of workstation 110 as shown in FIGS. 3b and 4-6. Such processing involves, per step 412, superimposing each outline 410 on a two-dimensional projection/radiographic image based on the cone-beam image 404 to form a treatment beam eye (BEV) view kV portal image such as shown in FIGS. 3b and 4b. Note that the kV portal image can be formed as a kV digital reconstructed radiographic (DRR) image for static patient anatomy verification or as a digital reconstructed fluoroscopic (DRF) image for verification of dynamic patient anatomy motion, such as respiratory motion. In either case, each kV portal image with corresponding outline 410 (FIG. 4b, for example) is compared with a treatment reference radiographic image (FIG. 4a, for example) that is generated according to the real-time radiation therapy plan to be executed. Should one or more areas of interest, such as a tumor or organ, of the kV portal image be displaced by at least a predetermined amount relative to the position of the corresponding area of interest of the reference image, then steps are taken to adjust the real-time radiation therapy plan for the day's treatment session. If the displacement is below the predetermined amount, then the real-time radiation plan is not adjusted.

In addition to the treatment dose, kV portal image can also be constructed for treatment recordation and verification as shown in FIGS. 3a-b. Further, organs of interest manifested on the CBCT image are auto-segmented and registered to the pre-treatment CT image. Therefore, daily and cumulative dose-volume relationships of each organ of interest can be created. In some implementations, a numerical filter is employed to estimate the final treatment dose in each organ of interest by performing parameter estimation for both stationary and non-stationary random processes of patient anatomical variation. Methods for sample estimation, such as the least square estimation, the principal component analysis (PCA) based estimation and singular value decomposition (SVD) estimation, may be implemented.

The estimation is then used to provide information for the treatment evaluation and plan modification decision to determine when to switch on the adaptive planning modification engine.

On-Line, Off-Line Image Guided Adaptive Radiation Therapy Planning

Figure 7:
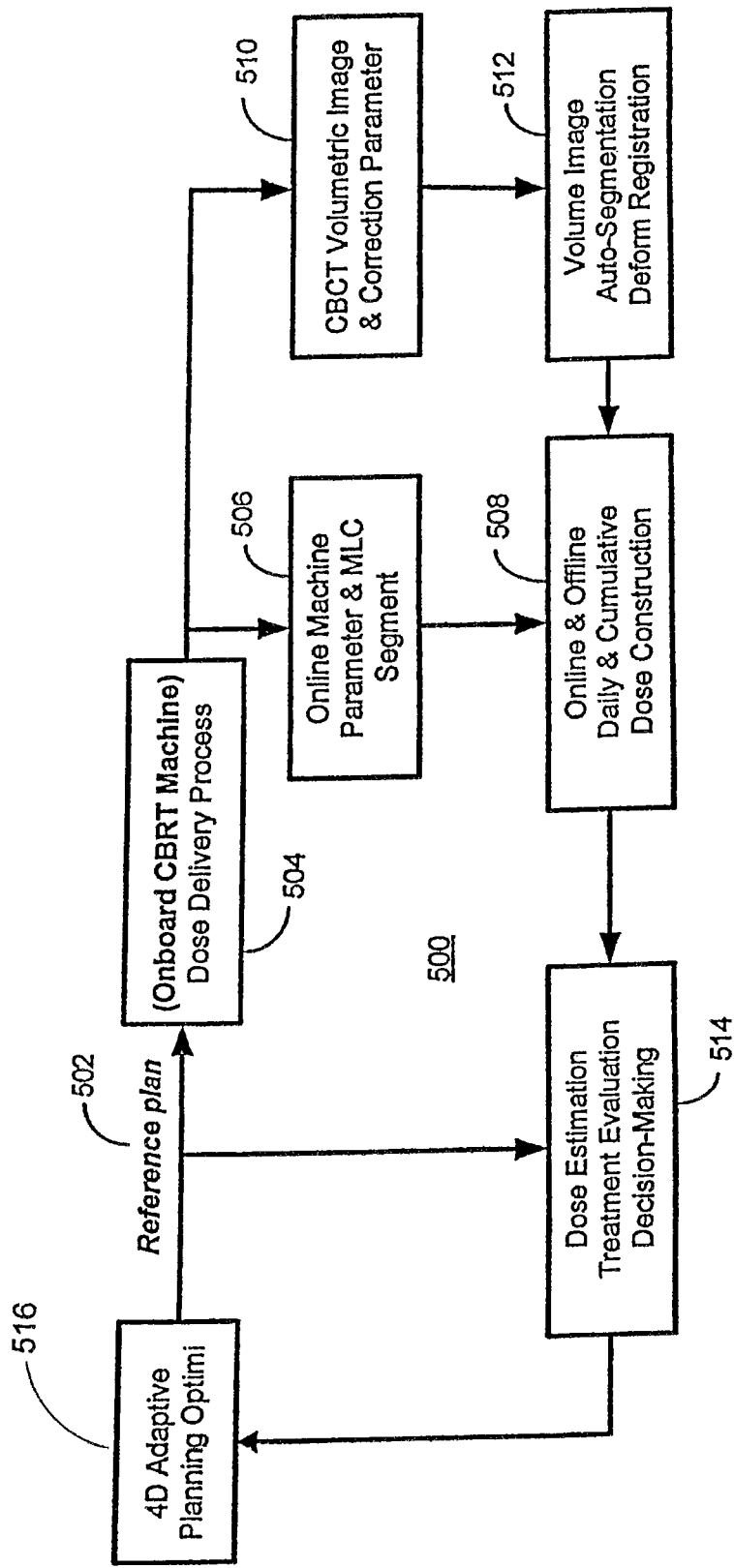
FIG. 7 shows an embodiment of a radiotherapy process to be used with the systems of FIGS. 1-2.

After the kV imaging process is completed, resulting in the initial radiation therapy plan being modified or retained, the patient is repositioned to receive radiation therapy per the modified/original reference plan and image guided adapted radiation therapy process 500 is performed as schematically shown in FIG. 7. In particular, the reference plan 502 is applied to the linear source 302 per process 504 so as to move the source 302 to a position designated in the reference plan 502 and to format parameters of the beam of radiation emitted from the source 302 as it impinges on the patient, such as angular position, beam energy and cross-sectional shape of the beam, in accordance with the reference plan 502. Such on-line and real-time parameters can be in the form of the angular position of the gantry 208, the angular orientation of the collimator 308, the positions of the leaves of the multi-leaf collimator 308, position of the table 306 and energy of the radiation beam. Process 504 can also involve moving individual leaves of a multi-leaf collimator 308 to desired positions per reference plan 502 so that that the radiation therapy beam generated by the linear source 302 is collimated so as to radiate a particular shaped area of the patient per the reference plan 502.

Once the reference plan 502 is implemented per process 504, the reference plan 502 can be altered to account for various factors that occur during the radiation therapy session. For example, the process 500 can entail having the system 100 monitor real-time, on-line machine treatment parameters of the linear source 302 and its radiation output online per process 506. The process 506 entails monitoring treatment parameters, such as beam angle, beam energy and cross-sectional shape of the beam. Such parameters can entail the position of the gantry, the angular position of the collimator 308, position of the leaves of the multi-leaf collimator 308, position of the table 306, the energy of the beam.

The real-time, on-line information obtained by the above mentioned monitoring process 506 is fed to workstation 112 of FIG. 1 so that it can be used during either the online and offline daily and cumulative dose construction process 508.

While a radiation therapy beam is applied to the patient per process 504, the area of interest to be treated is imaged via the cone-beam computed tomography system 200. The three-dimensional volumetric image is used to register and track various individual volumes of interest in a real-time and on-line manner. Prior to registration and tracking, a correction parameter must be determined by server 102 per process 510 so as to be applied to the volumetric image. The correction parameter is associated with the fact that rigid body components of the volumetric image are often not oriented in a preferred manner due to a number of factors, such as the position of the patient on the table 306 and the angular position of the collimator. Based on the measurement of those factors, a correction parameter is determined per process 510 that when applied to the three-dimensional image the image is re-oriented to a preferred position. The re-oriented three-dimensional image is stored at workstation 102 of FIG. 1. The workstation 102 contains a library of stored three-dimensional images of one or more areas of interest of the patient.

Once the correction parameter is determined, the segmentation-deformable organ registration workstation 110 receives the volumetric image generated by system 200 and correction parameter from server 102 via process 512. The workstation 110 executes process 512 so as to match the patient anatomical elements manifested on the volumetric image to those on the reference planning volumetric image associated with the reference plan. The image registration results are used to map the pre-treatment organ contours on the planning volumetric image commonly delineated by clinicians, to the corresponding points on the treatment volumetric image automatically. The registration methods applied for this process are quite standard such as the finite element method and the method of image similarity maximization. However, there have been number of modifications performed to optimize these methods for the specific applications of the CBCT image and organs of interest in radiotherapy, such as described in the publications: 1) Liang J., et al., "Reducing Uncertainties in Volumetric Image Based Deformable Organ Registration," Med Phys, 30(8), 2003, pp. 2116-2122, 2) Chi Y., et al., "Sensitivity Study on the Accuracy of Deformable Organ Registration Using Linear Biomechical Models," Med Phys, 33: (2006), pp. 421-33, 3) Zhang T., et al., "Automatic Delineation of Online Head and Neck CT Images: Towards Online Adaptive Radiotherapy," International Journal of Radiation Oncology Biology Physics, 68(2), (2007) pp. 522-30 and 4) Yan D., et al., "A Model to Accumulate Fractionated Dose in a Deforming Organ," International Journal of radiation Oncology, Biology Physics, 44(3): (1999), pp. 665-675, the entire contents of each of which is incorporated herein by reference.

Once each point in the volumetric image is tracked, that information is sent to workstation 112, which also receives the parameters per process 506. At workstation 112, an online daily and cumulative dose construction process 508 is performed. The daily dose construction process entails calculating/constructing for a real-time treatment the dose received for each volume of image data within the volumetric image tracked per process 512. After the treatment session for the day is completed, the daily dose for each volume of image data is stored in server 102. The daily dose for each volume of image data can be combined with daily doses for the same volumes of image data calculated/constructed from previous therapy sessions so that an accumulated dosage over time for each volume of image data is determined per process 508 and stored in server 102. Further details of the construction of the daily and cumulative treatment doses are discussed in the publications: 1) Yan D., et al., "A Model to Accumulate Fractionated Dose in a Deforming Organ," International Journal of radiation Oncology, Biology Physics, 44(3): (1999), pp. 665-675, 2) Yan D. et al. "Organ/Patient Geometric Variation in External Beam Radiotherapy and Its Effect," Medical Physics, 28(4), (2001), pp. 593-602 and 3) Lockman D., et al., "Estimating the Dose Variation in a Volume of Interest with Explicit Consideration of Patient Geometric Variation," Medical Physics, 27: (2000) pp. 2100-2108, the entire contents of each of which is incorporated herein by reference.

As shown in FIG. 7, treatment evaluation 514 is performed by workstation 114 following the patient organ registration and treatment dose construction processes 512 and 508, respectively. There are two purposes for treatment evaluation, (a) to determine if the current treatment delivery is the same as the one previously planned for the treatment quality assurance; and (b) to modify the ongoing treatment plan by including the patient anatomy/dose variations observed and quantified so far to optimize the treatment outcome. Such treatment evaluation 514 can be performed real-time, on-line and off-line.

Final treatment dose and outcome estimation are used to provide information for the treatment evaluation and plan modification decision to determine when to switch on the adaptive planning modification engine per process 514 of FIG. 7. A numerical filter is employed to estimate the final treatment dose in each organ of interest by performing parameter estimation for both stationary and non-stationary random processes of patient anatomical variation. Methods for sample estimation, such as the least-square estimation (LSE), the principal component analysis (PCA) based estimation and singular value decomposition (SVD) estimation, are implemented. The detail discussions of using these filters for organ geometry and dose estimation of different treatment sites have been discussed in the following documents: 1) Yan D. et al. "Organ/Patient Geometric Variation in External Beam Radiotherapy and Its Effect," Medical Physics, 28(4), (2001), pp. 593-602, 2) Lockman D., et al., "Estimating the Dose Variation in a Volume of Interest with Explicit Consideration of Patient Geometric Variation," Medical Physics, 27: (2000) pp. 2100-2108, 3) Sohn M. et al., "Modeling Individual Geometric Variation Based on Dominant Eigenmodes of Organ Deformation: Implementation and Evaluation," Phys Med Biol, 50: (2005) pp. 5893-908 and 4) Yan D., "Image-Guided/Adaptive Radiotherapy," Medical Radiology-Radiation Oncology, Volume: New Technologies in Radiation Oncology, Edited by W. Schlegel, T. Bortfeld and A L Grosu, Springer-Verlag Berlin Heidelberg New York Hong Kong, (2005) ISBN 3-540-00321-5, the entire contents of each of which is incorporated herein by reference.

The first task of treatment evaluation is related to treatment delivery and plan comparison performed by workstation 112 per process 514. If the comparison shows that the daily or cumulative treatment dosage for a particular subvolume of the image and the corresponding daily or cumulative planned dosages for the corresponding subvolume are outside of a certain tolerance (see, Yan D., et al., "A New Model for 'Accept Or Reject' Strategies in On-Line and Off-Line Treatment Evaluation," International Journal of Radiation Oncology, Biology Physics, 31(4): (1995) pp. 943-952, the entire contents of which are incorporated herein by reference.), then this means that the reference plan currently being implemented needs to be revised during the present therapy session. Note that the above described daily and cumulative dosages of a subvolume of interest can be tracked/displayed in time, such as on monitor 117 of FIG. 7 in a manner similar to the chart shown at the bottom of FIG. 5.

Figure 6:
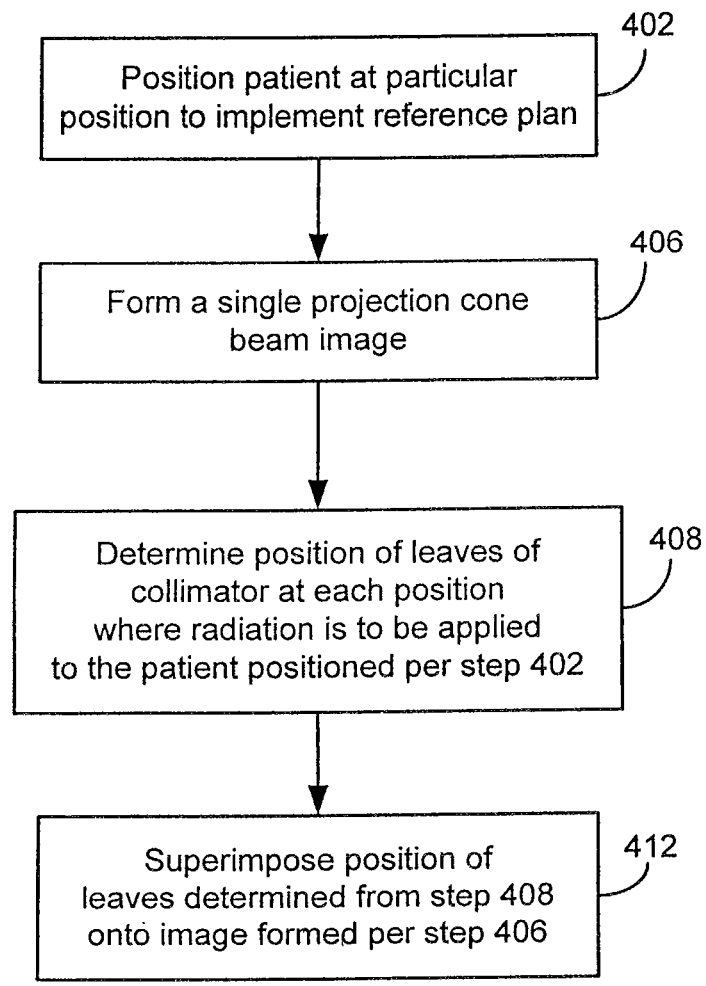
FIG. 6 is a flow diagram of a sequence of steps for forming either of the kV portal images of FIGS. 3-5.

Besides comparing the dosages, the positioning of areas to be treated with respect to the therapeutic beam is tested by forming a kV portal image per the previously described process of FIG. 6. If the real-time kV portal image is compared with a reference portal image and a subvolume of interest of the real-time kV portal image is found to be displaced in position or deformed in shape outside a certain tolerance with respect to a corresponding subvolume position in the reference portal image, then the reference plan, such as adjusting the leaves of the multi-leaf collimator, needs to be changed in this instance as well Note that the above described position of a subvolume of interest can be tracked/displayed in time as shown by the bottom chart of FIG. 5, wherein x, y and z positions of a particular subvolume is tracked from one daily treatment session to another daily treatment session.

If either of the comparisons described above are outside the corresponding tolerance, then a revision of the reference therapy treatment plan is performed in the on-line or off-line adaptive planning optimization process 516. Adaptive planning optimization is different than conventional radiotherapy planning where only pre-treatment computed tomographic image data is used. Instead, adaptive planning intends to utilize individual treatment history from patient anatomy/dose tracking as feedback to optimize treatment control parameters. Examples of techniques of adaptive planning optimization are described in the following publications: 1) Yan D., et al., "An Off-Line Strategy for Constructing a Patient-Specific Planning Target Volume for Image Guided Adaptive Radiotherapy of Prostate Cancer," International Journal of radiation Oncology, Biology Physics, 48(1), (2000) pp. 289-302, 2) Birkner M., et al., "Adapting Inverse Planning to Patient and Organ Geometrical Variation: Algorithm and Implementation," Med Phys, 30(10): (2003), pp. 2822-2831, 3) Yan D., "On-Line Adaptive Strategy for Dose Per Fraction Design," Proceeding, XIIIth International Conference on The Use of Computers in Radiotherapy, Heidelberg, Germany (2000), pp. 518-520 and 4) Yan D., et al., "Strategies for Off-Line and On-Line Image Feedback Adaptive Radiotherapy," Editors: B K Paliwal, D E Herbert, J F Fowler, M P Mehta, Biological & Physical Basis of IMRT & Tomotherapy, AAPM Symposium Proceeding No. 12, 2002, pp. 139-50.

Note that the above-described process regarding FIG. 7 can include real-time data/information by capturing data volumetric image data from system 200 and therapy beam parameter information during the time the therapy beam is generated. Such real-time information can be processed per processes 506, 508, 510, 512 and used in process 514 to determine if the therapy plan should be revised in "real-time." If it is so determined that revision is recommended, then the real-time data/information can be used in conjunction with prior dose information and position/shape information of the volume of interest determined from previous therapy sessions (off-line information) to reformulate the therapy plan.

While the above description demonstrates how "real-time" data/information can be used to revise a therapy plan via the process of FIG. 7, the description is equally applicable to non-real-time adaptive therapy. In this case, processes 506, 508, 510 and 512 use off-line information from previous treatment sessions and process 514 determines if a therapy plan to be used in the future should be revised. in "real-time."

In summary, the system 100 and process 500 provide volumetric image guided adaptive radiotherapy, which can be performed in real time, online and offline for treatment dose construction and feedback. Therefore, they provide all possible feedback information for image guided real time, online and offline radiotherapy. Thus, the system 100 and process 500 are able to fully utilize individual treatment information, which primarily includes the patient dose delivered in the previous treatment, patient anatomy in the present treatment and patient anatomy estimated for remaining treatment deliveries.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

We claim:

1. A system for radiotherapy comprising:
an imaging system that generates volumetric image data of an area of interest of an object, wherein said imaging system comprises a cone-beam computed tomography system comprising:
an x-ray source that emits x-rays towards said object;
a first detector for receiving x-rays penetrating through said area of interest of said object and generating signals to generate said volumetric image data of said area of interest of said object, wherein said first detector receives fan-shaped x-rays after they pass through said area of interest of said object, said first detector generating a first imaging signal for each of said received fan-shaped x-rays; and
a computer connected to said detector so as to receive said first imaging signals for each of said received fan-shaped x-rays, wherein said x-ray source and said first detector rotate about said object so that multiple imaging signals are reconstructed by said computer to generate a three-dimensional cone-beam computed tomography image therefrom;
a radiation source that emits a therapeutic radiation beam towards said area of interest of said object in accordance with a reference plan;
a second detector that receives radiation from said therapeutic radiation beam that passes through said area of interest, said second detector generating second imaging signals from said radiation; and
a processing system (a) that receives and evaluates said volumetric image data, said second imaging signals and at least one parameter of said therapeutic radiation beam to provide 1) a real-time evaluation of said reference plan and 2) a real-time modification of said reference plan, wherein real-time is defined to be a time period when said therapeutic radiation beam is emitted towards said area of interest of said object, (b) that constructs a treatment dose received in said area of interest, and c) that estimates a final treatment dose in said area of interest by performing parameter estimation for random processes of patient anatomical variation.

2. The system of claim 1, wherein said x-ray source comprises a kV x-ray source.

3. The system of claim 1, wherein said therapeutic radiation has an energy ranging from 4 MeV to 25 MeV.

4. The system of claim 1, wherein said reference plan specifies said area of said object to be exposed to said therapeutic radiation beam and a dosage said area of said object to be exposed to said therapeutic radiation beam is to receive from said radiation source during a single treatment session.

5. The system of claim 1, wherein said at least one parameter of said therapeutic radiation beam is selected from the group consisting of angle of said therapeutic radiation beam, energy of said therapeutic radiation beam and cross-sectional shape of said therapeutic radiation beam.

6. The system of claim 1, wherein said processing system comprises a workstation that performs a segmentation/registration process on said volumetric image data.

7. The system of claim 1, further comprising a workstation that compares said volumetric image data with a stored volumetric image taken from a previous volumetric image so that changes in movement and shape of each subvolume of said volumetric image data is tracked with respect to a corresponding subvolume of said stored volumetric image.

8. The system of claim 7, further comprising a second workstation that constructs a treatment dose received for each subvolume tracked by said workstation that compares said volumetric image data with said stored volumetric image.

9. The system of claim 8, further comprising a third workstation that compares said constructed treatment dose with a preferred treatment dose specified by said reference plan.

10. The system of claim 9, wherein if said constructed treatment dose and said preferred treatment dose are within a certain tolerance, then said reference plan is retained.

11. The system of claim 9, wherein if said constructed treatment dose and said preferred treatment dose are outside a certain tolerance, then said reference plan is altered.

12. The system of claim 11, wherein said reference plan is altered based on said real-time evaluation of said reference plan.

13. The system of claim 12, wherein said real-time modification of said reference plan is based on off-line information.

14. The system of claim 11, wherein said real-time modification of said reference plan is based on off-line information.

15. The system of claim 1, further comprising a workstation that constructs a treatment dose received for each subvolume in said area of interest.

16. The system of claim 15, further comprising a second workstation that compares said constructed treatment dose with a preferred treatment dose specified by said reference plan.

17. The system of claim 16, wherein if said constructed treatment dose and said preferred treatment dose are within a certain tolerance, then said reference plan is retained.

18. The system of claim 16, wherein if said constructed treatment dose and said preferred treatment dose are outside a certain tolerance, then said reference plan is altered.

19. The system of claim 18, wherein said reference plan is altered based on said real-time evaluation of said reference plan.

20. The system of claim 19, wherein said real-time modification of said reference plan is based on off-line information.

21. The system of claim 18, wherein said real-time modification of said reference plan is based on off-line information.

22. The system of claim 1, wherein said real-time evaluation and said real-time modification are performed in an on-line manner.

23. The system of claim 1, wherein said real-time evaluation and said real-time modification are performed in an off-line manner.

24. The system of claim 1, wherein the random processes of patient anatomical variation are stationary or non-stationary processes, or a combination thereof.

25. The system of claim 1, wherein the random processes of patient anatomical variation are non-stationary processes.

26. The system of claim 1, wherein the parameter estimation is based on the least square estimation, principal component analysis estimation, or singular value decomposition estimation, or any combination thereof.

27. A method of treating an object with radiation, comprising:
generating volumetric image data of an area of interest of an object, wherein said generating volumetric image data comprises:
emitting x-rays towards said object; and
detecting x-rays penetrating through said area of interest of said object and generating signals to generate said volumetric image data of said area of interest of said object;

emitting a therapeutic radiation beam towards said area of interest of said object in accordance with a reference plan;

generating an image based on said therapeutic radiation beam;

evaluating said volumetric image data, said image based on said therapeutic beam, and at least one parameter of said therapeutic radiation beam to provide 1) a real-time evaluation of said reference plan and 2) a real-time modification of said reference plan, wherein real-time is defined to be a time period when said therapeutic radiation beam is emitted towards said area of interest of said object;

constructing a treatment dose received in said area of interest; and estimating a final treatment dose in said area of interest by performing parameter estimation for random processes of patient anatomical variation.

28. The method of claim 27, wherein said reference plan specifies said area of said object to be exposed to said therapeutic radiation beam and a dosage said area of said object to be exposed to said therapeutic radiation beam is to receive from said radiation source during a single treatment session.

29. The method of claim 27, wherein said at least one parameter of said therapeutic radiation beam is selected from the group consisting of angle of said therapeutic radiation beam, energy of said therapeutic radiation beam and cross-sectional shape of said therapeutic radiation beam.

30. The method of claim 27, wherein said evaluating comprises performing a segmentation/registration process on said volumetric image data.

31. The method of claim 27, further comprising comparing said volumetric image data with a stored volumetric image taken from a previous volumetric image so that changes in movement and shape of each subvolume of said volumetric image data is tracked with respect to a corresponding subvolume of said stored volumetric image.

32. The method of claim 31, further comprising constructing a treatment dose received for each subvolume tracked.

33. The method of claim 32, further comprising comparing said constructed treatment dose with a preferred treatment dose specified by said reference plan.

34. The method of claim 33, wherein if said constructed treatment dose and said preferred treatment dose are within a certain tolerance, then said reference plan is retained.

35. The method of claim 33, wherein if said constructed treatment dose and said preferred treatment dose are outside a certain tolerance, then said reference plan is altered.

36. The method of claim 35, wherein said reference plan is altered based on said real-time evaluation of said reference plan.

37. The method of claim 36, wherein said real-time modification of said reference plan is based on off-line information.

38. The method of claim 35, wherein said real-time modification of said reference plan is based on off-line information.

39. The method of claim 27, wherein said real-time evaluation and said real-time modification are performed in an on-line manner.

40. The method of claim 27, wherein said real-time evaluation and said real-time modification are performed in an off-line manner.

41. The method of claim 27, wherein the random processes of patient anatomical variation are stationary or non-stationary processes, or a combination thereof.

42. The method of claim 27, wherein the random processes of patient anatomical variation are non-stationary processes.

43. The method of claim 27, wherein the parameter estimation is based on the least square estimation, principal component analysis estimation, or singular value decomposition estimation, or any combination thereof.

44. A planning and control system for radiotherapy comprising:

a system that captures and evaluates parameters of a volumetric image of an area of interest of an object, a therapeutic radiation beam directed towards said area of interest of said object in accordance with a reference plan, and an image of said area of interest formed from said therapeutic radiation beam so as to provide 1) a real-time evaluation of said reference plan and 2) a real-time modification of said reference plan, wherein real-time is defined to be a time period when said therapeutic radiation beam is emitted towards said area of interest of said object, wherein said system constructs a treatment dose based on said captured parameters of said volumetric image and said therapeutic radiation beam and estimates a final treatment dose in said area of interest by performing parameter estimation for random processes of patient anatomical variation; and a monitor that displays information based on one or more of the captured parameters of said volumetric image and said therapeutic radiation beam.

45. The planning and control system of claim 44, further comprising a processor that identifies and registers each subvolume of image data within said volumetric image.

46. The planning and control system of claim 45, further comprising a second processor that constructs a treatment dose for each of said volume of image data based on said captured parameters of said volumetric image and said therapeutic radiation beam.

47. The planning and control system of claim 46, wherein said treatment dose is a daily treatment dose.

48. The planning and control system of claim 46, wherein said treatment dose is a cumulative treatment dose.

49. The planning and control system of claim 46, further comprising a third processor that performs a 4D adaptive planning process that adjusts radiation therapy treatment of said area of interest for a particular day in a real-time manner based on said real-time evaluation.

50. The planning and control system of claim 49, wherein said third processor adjusts said radiation therapy treatment of said area of interest based on a comparison of a real-time position or shape of said subvolume of image data and a planned position or shape of a corresponding subvolume of image data.

51. The planning and control system of claim 49, wherein said third processor adjusts said radiation therapy treatment of said area of interest based on a comparison of said treatment dose and a planned treatment dose.

52. The planning and control system of claim 44, wherein said treatment dose is a daily treatment dose.

53. The planning and control system of claim 44, wherein said treatment dose is a cumulative treatment dose.

54. The planning and control system of claim 44, further comprising a processor that performs a 4D adaptive planning process that adjusts radiation therapy treatment of said area of interest for a particular day in a real-time manner based on said real-time evaluation.

55. The planning and control system of claim 45, wherein said processor adjusts therapy treatment of said area of interest based on a comparison of a real-time position or shape of said object within said area of interest and a planned position or shape of said object.

56. The planning and control system of claim 44, wherein said processor adjusts therapy treatment of said area of interest based on a comparison of a real-time treatment dose of said object within said area of interest and a planned treatment dose of said object.

57. The planning and control system of claim 44, wherein said real-time evaluation and said real-time modification are performed in an on-line manner.

58. The planning and control system of claim 44, wherein said real-time evaluation and said real-time modification are performed in an off-line manner.

59. The system of claim 44, wherein the random processes of patient anatomical variation are stationary or non-stationary processes, or a combination thereof.

60. The system of claim 44, wherein the random processes of patient anatomical variation are non-stationary processes.

61. The system of claim 44, wherein the parameter estimation is based on the least square estimation, principal component analysis estimation, or singular value decomposition estimation, or any combination thereof.

62. A method of planning and controlling a radiation therapy session, the method comprising:
    capturing and evaluating parameters of a volumetric image of an area of interest of an object, a therapeutic radiation beam directed towards said area of interest of said object in accordance with a reference plan, and an image of said area of interest formed from said therapeutic radiation beam so as to provide 1) a real-time evaluation and 2) a real-time modification of said reference plan, wherein real-time is defined to be a time period when said therapeutic radiation beam is emitted towards said area of interest of said object;
    planning and controlling a radiation therapy session based on said real-time evaluation;
    displaying information based on one or more of said captured parameters of said volumetric image and said therapeutic radiation beam;
    constructing a treatment dose based on said captured parameters of said volumetric image and said therapeutic radiation beam; and
    estimating a final treatment dose in said area of interest by performing parameter estimation for random processes of patient anatomical variation.

63. The method of claim 62, further comprising identifying and registering each subvolume of image data within said volumetric image.

64. The method of claim 63, further comprising constructing a treatment dose for each of said identified and registered subvolumes of image data based on said captured parameters of said volumetric image and said therapeutic radiation beam.

65. The method of claim 62, further comprising performing a 4D adaptive planning process that adjusts radiation therapy treatment of said area of interest for a particular day in a real-time manner based on said real-time evaluation.

66. The method of claim 65, wherein said performing comprises adjusting said radiation therapy treatment based on a comparison of a real-time position or shape of said object within said area of interest and a planned position or shape of said object.

67. The method of claim 65, wherein said performing comprises adjusting said radiation therapy treatment based on a comparison of a real-time treatment dose of said object within said area of interest and a planned treatment dose of said object.

68. The method of claim 65, wherein said real-time modification of said reference plan is based on off-line information.

69. The method of claim 62, wherein said real-time modification of said reference plan is based on off-line information.

70. The method of claim 62, wherein said real-time evaluation and said real-time modification are performed in an on-line manner.

71. The method of claim 62, wherein said real-time evaluation and said real-time modification are performed in an off-line manner.

72. The method of claim 62, wherein the random processes of patient anatomical variation are stationary or non-stationary processes, or a combination thereof.

73. The method of claim 62, wherein the random processes of patient anatomical variation are non-stationary processes.

74. The method of claim 62, wherein the parameter estimation is based on the least square estimation, principal component analysis estimation, or singular value decomposition estimation, or any combination thereof.

75. A system for radiotherapy comprising:
    a radiation source that is programmed to emit a therapeutic radiation beam towards an area of interest of an object in accordance with a reference plan during a real-time time period when said object is on-line;
    a first imaging system that generates on-line volumetric image data of said area of interest of said object during said real-time time period when said object is on-line, and off-line volumetric image data of said area of interest of said object during a non-real time off-line time period, wherein real-time is defined to be a time period when said therapeutic radiation beam is emitted towards said area of interest of said object;
    a second imaging system that generates an image based on said therapeutic radiation beam; and
    a processing system (a) that receives and processes said image based on said therapeutic radiation beam and one or more of said on-line and off-line volumetric image data to alter said reference plan, (b) that constructs a treatment dose received in said area of interest, and (c) that estimates a final treatment dose in said area of interest by performing parameter estimation for random processes of patient anatomical variation.

76. The system of claim 75, wherein said processing system processes said on-line volumetric image data to alter said reference plan.

77. The system of claim 76, wherein said processing system processes said off-line volumetric image data to alter said reference plan.

78. The system of claim 75, wherein said processing system processes said off-line volumetric image data to alter said reference plan.

79. The system of claim 75, wherein the random processes of patient anatomical variation are stationary or non-stationary processes, or a combination thereof.

80. The system of claim 75, wherein the random processes of patient anatomical variation are non-stationary processes.

81. The system of claim 75, wherein the parameter estimation is based on the least square estimation, principal component analysis estimation, or singular value decomposition estimation, or any combination thereof.

82. A method of treating an object with radiation, comprising:
- planning on emitting a therapeutic radiation beam towards an area of interest of an object in accordance with a reference plan during a real-time time period when said object is on-line;
- generating on-line volumetric image data of said area of interest of said object during said real-time time period when said object is on-line, and off-line volumetric image data of said area of interest of said object during a non-real time off-line time period, wherein real-time period is defined to be a time period when said therapeutic radiation beam is emitted towards said area of interest of said object;
- generating an image based on said therapeutic radiation beam;
- altering said reference plan based on said image based on said therapeutic radiation beam and one or more of said on-line and off-line volumetric image data;
- constructing a treatment dose received in said area of interest; and
- estimating a final treatment dose in said area of interest by performing parameter estimation for random processes of patient anatomical variation.

83. The method of claim 82, wherein said altering is based on said on-line volumetric image data.

84. The method of claim 83, wherein said altering is based on said off-line volumetric image data.

85. The method of claim 82, wherein said altering is based on said off-line volumetric image data.

86. The method of claim 82, wherein the random processes of patient anatomical variation are stationary or non-stationary processes, or a combination thereof.

87. The method of claim 82, wherein the random processes of patient anatomical variation are non-stationary processes.

88. The method of claim 82, wherein the parameter estimation is based on the least square estimation, principal component analysis estimation, or singular value decomposition estimation, or any combination thereof.

* * * * *